United States Patent
Elkins et al.

(10) Patent No.: US 7,862,558 B2
(45) Date of Patent: *Jan. 4, 2011

(54) SUBDERMAL CRYOGENIC REMODELING OF MUSCLES, NERVES, CONNECTIVE TISSUE, AND/OR ADIPOSE TISSUE (FAT)

(75) Inventors: Lisa Elkins, Woodside, CA (US); Ronald Williams, Menlo Park, CA (US)

(73) Assignee: MyoScience, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/399,598

(22) Filed: Mar. 6, 2009

(65) Prior Publication Data

US 2009/0171334 A1 Jul. 2, 2009

Related U.S. Application Data

(63) Continuation of application No. 11/770,185, filed on Jun. 28, 2007, which is a continuation-in-part of application No. 11/295,204, filed on Dec. 5, 2005.

(60) Provisional application No. 60/683,393, filed on May 20, 2005.

(51) Int. Cl.
*A61B 18/02* (2006.01)
(52) U.S. Cl. .............. 606/24; 606/20; 606/21; 606/23; 606/25
(58) Field of Classification Search ............ 606/20–26; 607/105, 107, 113
See application file for complete search history.

(56) References Cited

U.S. PATENT DOCUMENTS

| | | | |
|---|---|---|---|
| 2,319,542 A | 5/1943 | Hall | |
| 2,672,032 A | 3/1954 | Towse | |
| 3,226,492 A | 12/1965 | Steinberg | |

(Continued)

FOREIGN PATENT DOCUMENTS

CA 2 643 474 9/2007

(Continued)

OTHER PUBLICATIONS

Advanced Cosmetic Intervention, Inc. [webpage], retrieved from the Internet: <<http://www.acisurgery.com>>, copyright 2007, 1 page.

(Continued)

*Primary Examiner*—Linda C Dvorak
*Assistant Examiner*—Jaymi Della
(74) *Attorney, Agent, or Firm*—Townsend and Townsend and Crew LLP

(57) ABSTRACT

Devices, systems, and methods treat cosmetic defects, and often apply cooling with at least one tissue-penetrating probe inserted through of the skin of a patient. The cooling may remodel one or more target tissue so as to effect a desired change in a composition of the target tissue and/or a change in its behavior. Exemplary embodiments of the cooling treatments will interfere with the nerve/muscle contractile function chain so as to mitigate wrinkles of the skin. Related treatments may be used therapeutically for treatment of back and other muscle spasms, chronic pain, and the like. Some embodiments may remodel subcutaneous adipose tissue so as to alter a shape or appearance of the skin surface.

15 Claims, 21 Drawing Sheets

U.S. PATENT DOCUMENTS

| | | | |
|---|---|---|---|
| 3,343,544 A * | 9/1967 | Dunn et al. | 606/25 |
| 3,507,283 A | 4/1970 | Thomas, Jr. | |
| 3,532,094 A * | 10/1970 | Stahl | 606/25 |
| 3,664,344 A | 5/1972 | Bryne | |
| 3,886,945 A | 6/1975 | Stumpf et al. | |
| 3,889,681 A | 6/1975 | Waller et al. | |
| 3,951,152 A | 4/1976 | Crandell et al. | |
| 3,993,075 A | 11/1976 | Lisenbee et al. | |
| 4,140,109 A | 2/1979 | Savic et al. | |
| 4,207,897 A | 6/1980 | Lloyd et al. | |
| 4,306,568 A | 12/1981 | Torre | |
| 4,376,376 A | 3/1983 | Gregory | |
| 4,404,862 A * | 9/1983 | Harris, Sr. | 73/864.16 |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,200,170 A | 4/1993 | McDow | |
| 5,294,325 A * | 3/1994 | Liu | 204/418 |
| 5,334,181 A | 8/1994 | Rubinsky et al. | |
| 5,571,147 A | 11/1996 | Sluijter et al. | |
| 5,647,868 A | 7/1997 | Chinn | |
| 5,755,753 A | 5/1998 | Knowlton | |
| 5,814,040 A | 9/1998 | Nelson et al. | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A | 3/2000 | Rubinsky | |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,182,666 B1 * | 2/2001 | Dobak, III | 128/898 |
| 6,196,839 B1 | 3/2001 | Ross | |
| 6,277,116 B1 | 8/2001 | Utely et al. | |
| 6,432,102 B2 | 8/2002 | Joye et al. | |
| 6,494,844 B1 | 12/2002 | Van Bladel et al. | |
| 6,503,246 B1 | 1/2003 | Har-Shai et al. | |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,648,880 B2 | 11/2003 | Chauvet et al. | |
| 6,669,688 B2 | 12/2003 | Svaasand et al. | |
| 6,672,095 B1 | 1/2004 | Luo | |
| 6,706,037 B2 | 3/2004 | Zvuloni et al. | |
| 6,723,092 B2 * | 4/2004 | Brown et al. | 606/41 |
| 6,749,624 B2 | 6/2004 | Knowlton | |
| 6,761,715 B2 | 7/2004 | Carroll | |
| 6,764,493 B1 | 7/2004 | Weber et al. | |
| 6,786,902 B1 | 9/2004 | Rabin et al. | |
| 6,789,545 B2 | 9/2004 | Littrup et al. | |
| 6,858,025 B2 | 2/2005 | Maurice | |
| 6,905,492 B2 | 6/2005 | Zvuloni et al. | |
| 7,081,111 B2 | 7/2006 | Svaasand et al. | |
| 7,083,612 B2 | 8/2006 | Littrup et al. | |
| 7,250,046 B1 | 7/2007 | Fallat | |
| 7,367,341 B2 | 5/2008 | Anderson et al. | |
| 2002/0013602 A1 | 1/2002 | Huttner | |
| 2002/0049436 A1 * | 4/2002 | Zvuloni et al. | 606/21 |
| 2002/0068929 A1 * | 6/2002 | Zvuloni | 606/22 |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0181896 A1 | 9/2003 | Zvuloni et al. | |
| 2003/0220674 A1 * | 11/2003 | Anderson et al. | 607/96 |
| 2004/0122482 A1 | 6/2004 | Tung et al. | |
| 2004/0162551 A1 | 8/2004 | Brown et al. | |
| 2004/0167505 A1 | 8/2004 | Joye et al. | |
| 2004/0191229 A1 | 9/2004 | Link et al. | |
| 2004/0204705 A1 | 10/2004 | Lafontaine | |
| 2004/0210212 A1 | 10/2004 | Maurice | |
| 2004/0215178 A1 | 10/2004 | Maurice | |
| 2004/0215294 A1 | 10/2004 | Littrup et al. | |
| 2004/0225276 A1 | 11/2004 | Burgess | |
| 2004/0243116 A1 | 12/2004 | Joye et al. | |
| 2004/0267257 A1 * | 12/2004 | Bourne et al. | 606/41 |
| 2005/0177147 A1 | 8/2005 | Vancelette et al. | |
| 2005/0177148 A1 | 8/2005 | van der Walt et al. | |
| 2005/0203505 A1 | 9/2005 | Megerman et al. | |
| 2005/0203593 A1 | 9/2005 | Shanks | |
| 2005/0209565 A1 | 9/2005 | Yuzhakov et al. | |
| 2005/0209587 A1 | 9/2005 | Joye et al. | |
| 2005/0228288 A1 | 10/2005 | Hurst | |
| 2005/0261753 A1 | 11/2005 | Littrup et al. | |
| 2005/0276759 A1 | 12/2005 | Roser et al. | |
| 2005/0283148 A1 | 12/2005 | Janssen et al. | |
| 2006/0009712 A1 | 1/2006 | Van Bladel et al. | |
| 2006/0015092 A1 | 1/2006 | Joye et al. | |
| 2006/0069385 A1 | 3/2006 | Lafontaine et al. | |
| 2006/0084962 A1 | 4/2006 | Joye et al. | |
| 2006/0129142 A1 | 6/2006 | Reynolds | |
| 2006/0189968 A1 | 8/2006 | Howlett et al. | |
| 2006/0200117 A1 | 9/2006 | Hermans | |
| 2006/0212028 A1 | 9/2006 | Joye et al. | |
| 2006/0223052 A1 | 10/2006 | MacDonald et al. | |
| 2007/0060921 A1 | 3/2007 | Janssen et al. | |
| 2007/0088217 A1 | 4/2007 | Babaev | |
| 2007/0129714 A1 | 6/2007 | Elkins et al. | |
| 2007/0156125 A1 | 7/2007 | DeLonzor | |
| 2007/0161975 A1 | 7/2007 | Goulko | |
| 2007/0167943 A1 | 7/2007 | Janssen et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0154254 A1 | 6/2008 | Burger et al. | |
| 2008/0183164 A1 | 7/2008 | Elkins et al. | |
| 2008/0200910 A1 | 8/2008 | Burger et al. | |
| 2008/0287839 A1 | 11/2008 | Rosen et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0248001 A1 | 10/2009 | Burger et al. | |

FOREIGN PATENT DOCUMENTS

| | | | |
|---|---|---|---|
| EP | 0 043 447 A2 | | 6/1981 |
| EP | 1 377 327 B1 | | 9/2007 |
| GB | 1402632 | | 8/1975 |
| JP | 10-014656 | | 1/1998 |
| JP | 2006-130055 | | 5/2006 |
| WO | WO 97/49344 | | 12/1997 |
| WO | WO 01/97702 | | 12/2001 |
| WO | 2004/045434 | * | 6/2004 |
| WO | WO 2004045434 | * | 6/2004 |
| WO | WO 2004/089460 | | 10/2004 |
| WO | WO 2005/000106 | | 1/2005 |
| WO | WO 2006/012128 | | 2/2006 |
| WO | WO 2006/023348 | | 3/2006 |
| WO | WO 2006/125835 | | 11/2006 |
| WO | WO 2007/037326 | | 4/2007 |
| WO | WO 2007/089603 | | 8/2007 |
| WO | WO 2007/129121 | | 11/2007 |
| WO | WO 2007/135629 | | 11/2007 |

| | | |
|---|---|---|
| WO | WO 2009/026471 | 2/2009 |

OTHER PUBLICATIONS

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

Cryosurgical Concepts, Inc., [webpage] "CryoProbe™", retrieved from the Internet: <<http://www.cyro-surgical.com//>> on Feb. 8, 2002, 2 pages total.

Har-Shai et al., "Effect of skin surface temperature on skin pigmentation during contact and intralesional cyrosurgery of hypertrophic scars and Kleoids," Journal of the European Academy of Dermatology and Venereology 21 (2), 191-198.

One Med Group, LLC., [wepage] "CryoProbe™", retrieved from the Internet: <<http://www.onemedgroup.com/>> on Feb. 8, 2002, 2 pages total.

Utley et al., "Radiofrequency Ablation of the Nerve to the Corrugator Muscle for the Elimination of Glabellar Furrowing," Arch. Facieal Plastic Surgery 1: 46-48, 1999.

Yang et al., "Apoptosis induced by cryo-injury in human colorectal cancer cells is associated with mitochondrial dysfunction.," Int J Cancer. Jan. 20, 2003;103(3):360-369.

Dasiou-Plankida, "Fat injections for facial rejuvenation: 17 years experience in 1720 patients," Journal of Cosmetic Dermatology, Oct. 22, 2004; 2(3-4): 119-125.

Extended European Search Report and Search Opinion of EP Application No. 06770671.3, mailed Sep. 22, 2009, 14 pages total.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

* cited by examiner

  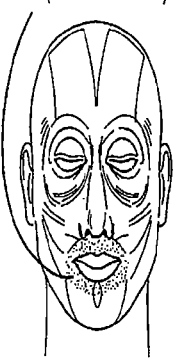 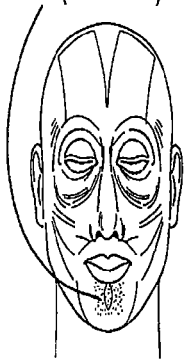 
FIG. 2C    FIG. 2D    FIG. 2E    FIG. 2F    FIG. 2G
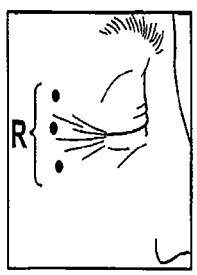 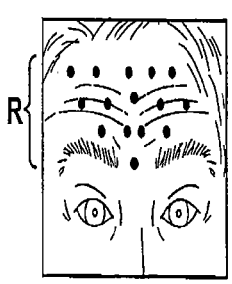 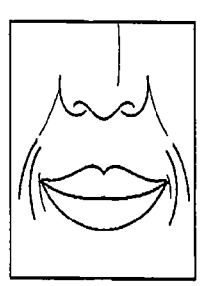  
FIG. 2H    FIG. 2I    FIG. 2J    FIG. 2K    FIG. 2L

SUBDERMAL CRYOGENIC REMODELING OF MUSCLES, NERVES, CONNECTIVE TISSUE, AND/OR ADIPOSE TISSUE (FAT)

CROSS REFERENCES TO RELATED APPLICATIONS

This application is a continuation of U.S. patent application Ser. No. 11/770,185, filed Jun. 28, 2007, which is a continuation-in-part of U.S. patent application Ser. No. 11/295,204, filed Dec. 5, 2005, which claims the benefit of U.S. Provisional Patent Application No. 60/683,393, filed May 20, 2005, the entire disclosures of which are incorporated herein by reference.

BACKGROUND OF THE INVENTION

The present invention is generally directed to medical devices, systems, and methods, particularly for improving the appearance of a patient and other applications. Applications can be therapeutic in nature as well as cosmetic. Embodiments of the invention include devices, systems, and methods for applying cryogenic energy to subcutaneous tissues so as to selectively remodel one or more target tissues below an exposed surface of the skin, often by inhibiting undesirable and/or unsightly effects on the skin (such as lines, wrinkles, or cellulite dimples) or on other surrounding tissue. The remodeling of the target tissue may achieve a desired change in its behavior or composition, and will often help alleviate cosmetically undesirable characteristics.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary denervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing, e.g., via collagen enhancement; or enhancement can also be achieved via collagen or other injectable. Development of non-pharmacologically based cosmetic treatments also continues. For example, endermology is a mechanical based therapy that utilizes vacuum suction to stretch or loosen fibrous connective tissues which are implicated in the dimpled appearance of cellulite. Other examples include transdermal ultrasound, which is used to reduce fat mass, and several types of energy (e.g., RF) used to promote collagen building and skin tightening.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, it would be desirable to provide improved medical devices, systems, and methods, particularly for treatment of wrinkles, fat, cellulite, and other cosmetic defects, as well as some therapeutic effects such as treatment of lesions (e.g., malignant, benign, etc.), acute or chronic pain, etc. It would be particularly desirable if these new techniques provided an alternative visual appearance improvement and/or treatment mechanism which could replace and/or compliment known bioactive and other cosmetic therapies, ideally allowing patients to decrease or eliminate the injection of toxins and harmful cocktails or pharmaceuticals while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time".

BRIEF SUMMARY OF THE INVENTION

The present invention generally provides improved medical devices, systems, and methods for the treatment of cosmetic defects and other applications, e.g., therapeutic applications. Embodiments of the present invention apply cooling with at least one probe inserted through an exposed surface of the skin of a patient. The cooling may remodel one or more target tissue so as to effect a desired change in a composition of the target tissue and/or a change in its behavior. Exemplary embodiments of the cooling treatments will interfere with the nerve/muscle contractile function chain so as to mitigate wrinkles of the skin, and related treatments may be used therapeutically for treatment of back and other muscle spasms, chronic pain, and the like. Some embodiments may remodel subcutaneous adipose tissue or fibrous connective tissue so as to alter a shape or appearance of the skin surface.

Optionally, cooling times, temperatures, pressures, cooling fluid vaporization or the like may be configured to provide a desired or variably selectable efficacy time. Treatments at moderate temperatures (for example at temperatures which only temporarily stun tissues but do not induce significant apoptosis or necrosis) may have only short term muscle contraction inhibiting effects. Other treatments may be longer lasting, optionally being permanent. Fibroblastic response-based efficacy may, in some embodiments, be self-limiting. Probe, applicator, and/or controller designs may allow treatments by persons with limited skill and training, so that efficacy is not operator dependent. In some embodiments, no foreign bodies and/or materials will be left behind. Other embodiments may employ materials such as bioactive agents, warmed saline, or the like to limit injury and/or enhance remodeling efficacy, with some treatments being combined with pharmaceuticals such as BOTOX® compounds or the like. Similarly, no tissue will be required to be removed to achieve the desired affect in many embodiments. Advantageously, the cooling probe, a single-use cooling fluid cartridge, and controller may be included in a disposable (often non-sterilizable) self-contained treatment system that may limit capital investment and facilitate treatments in third-world environments.

In a first aspect, the invention provides a method for improving a cosmetic appearance of a patient. The patient has a skin surface, and the method comprises inserting a probe through the skin surface and cooling a target tissue below the skin surface such that the target tissue is remodeled. The remodeling of the target tissue alters a shape of the skin surface.

In many cases, prior to remodeling the skin surface will exhibit lines or wrinkles. Contraction of sub-dermal muscles and the associated movement of the skin may contribute to the development and appearance of these lines or wrinkles, and the remodeling can be performed so as to reduce or eliminate this contraction and/or movement, effectively smoothing the lines or wrinkles. The skin surface will often include a region of the face, with the target tissues optionally comprising a muscle, a nerve, connective tissue, nerve/muscle junction, and/or the like associated with that muscle. The cooling may inhibit contraction of the muscle so as to improve an appearance of the patient.

In many embodiments, a cooling-induced injury of the skin surface may be inhibited such that the target tissue is selectively cooled. For example, warming energy may be applied along the skin surface, optionally by heating the skin surface with an applicator of the probe before, during, and/or after cooling of the target tissue. A material which inhibits cooling injury may also be disposed along the skin surface during cooling, such as a heated biocompatible fluid, a biocompatible cryoprotectant (optionally comprising dimethylsulfoxide ("DMSO"), propylene glycol, and/or glycerol). In some embodiments, injury to the skin surface may be inhibited by applying a cooling injury inhibiting or reducing material to the target tissue so that overall cooling and damage to the skin may be limited. It will often be desirable to limit injury to the skin surface sufficiently to avoid permanently altering a color of the skin surface, and/or to limit or avoid visible necrosis of the dermal tissues along the skin surface, or other visible marks or damage (e.g., bruising or blistering).

In some embodiments, the skin surface may have an uneven cellulite or other adipose tissue-induced texture and/or shape. The remodeling may be performed so as to smooth such a texture so as to improve the appearance of the patient. Optionally, the cooling may be performed so as to induce a reduction in tissue mass, e.g., after removal of the probe from the patient. The reduction in tissue mass may occur as part of a tissue response to the cooling, optionally as part of the healing process, and the reduction in tissue mass may at least help provide a desired change in the shape of the skin surface. For example, where the tissue comprises an adipose tissue, a healing response to the cooling may decrease a mass of the adipose tissue by inducing adipose tissue restoration. In other embodiments, the cooling may reduce muscle mass, particularly of muscles of the face which are associated with lines and wrinkles.

In general, the target tissue may be cooled to a temperature from about 10° C. to about −40° C., with the target tissue optionally being cooled to a temperature in a range from about 0° C. to about −15° C., as well as temperatures below about −15° C., including a temperature in a range from about 0° C. to about −20° C. More moderate treatment temperatures (for example, warmer than about −5° C.) and briefer treatment times may provide temporary efficacy, while colder treatment temperatures (for example, at about −5° C. or cooler) and longer treatment times may result in permanent changes to the target tissue and/or skin surface shape. Surprisingly, within some treatment temperature ranges, warmer treatments may provide more long-term or even permanent efficacy, while colder treatment temperatures may result in temporary changes to the target tissue and skin surface shape. For example, in some embodiments long-term or permanent efficacy of the treatment may be provided through apoptosis (sometimes referred to as programmed cell death). In contrast, necrosis-based effects may be reduced or eliminated with healing. Apoptosis can reduce muscle mass or disrupt the chain of contractility without inducing inflammation and triggering of the satellite cells that may be involved in the skeletal muscle repair process. Alternative mechanisms may also be involved, including a temporary and/or permanent loss of elasticity in muscle tissues through changes in morphology of collagen and/or elastin with ice formation, necrosis, a loss of elasticity in the fibrous connective tissue, impairment of signal transmission along the neural pathways, blocking production of acetylcholine (or other chemicals pertinent to contractility) or disrupting conductivity, hypoxia (optionally by cutting-off of the blood supply to a muscle or other tissue in the contractile chain through apoptosis or some other mechanism), or the like.

Advantageously, a permanent or temporary effect may be selected, with even the duration of the effect optionally being selected by the patient and/or system user, allowing (for example) an initially temporary treatment to be performed so as to verify the desirability of the results prior to implementing a long lasting or permanent treatment. In some embodiments, smaller doses or regions of a more permanent effect may be delivered sequentially over time in order to achieve a permanent, full effect desired while avoiding drastic, over dosed, or undesirable outcomes.

In many embodiments, a plurality of tissue-penetrating probes may be inserted through the skin surface. Optionally, a separation between adjacent probes may be established so that a cooling effect remodels a desired portion, the majority of, substantially all of, and/or all of the tissues disposed between the probes. Varied amounts of tissue and/or patterns of targeted tissues can provide different desired effects, with the targeted tissues optionally being treated sequentially using a single tissue penetrating probe or the like.

In another aspect, the invention provides a method for improving a cosmetic appearance of a patient. The patient has a skin surface with a muscle therebelow. The muscle has an associated nerve/muscle contractile chain. The chain typically includes, for example, the muscle, a nerve, a connective tissue (such as a ligament, tendon, cartilage, or the like), and/or a nerve/muscle junction, and can also encompass related tissues such as the blood vessels which supply blood to the muscles or the like. The method comprises directing energy or cooling from a probe to a component of the nerve/muscle contractile chain such that the component is remodeled and the remodeling inhibits contraction of the muscle so as to improve the cosmetic appearance of the skin surface.

In yet another aspect, the invention provides a method for enhancing or increasing muscle contractility or contractile function. In some instances, for example, cooling of tissue according to methods described herein can be selected so as to stimulate tissue growth and tissue remodeling within the target tissue. For example, the cooling may stimulate activation, recruitment, and/or proliferation of certain cells, such as muscle progenitor cells. Resulting stimulated muscle building or increased muscle contractility can be induced so as to improve the cosmetic appearance of the patient, including improving skin surface texture or tightening a skin surface. In certain embodiments, stimulation of muscle building and/or increased contractility, as described above, may be used to counter asymmetry in a target tissue, either existing or treatment induced, such as to repair or improve an undesired outcome of a treatment to reduce muscle contractility. For example, cooling of the target tissue as described herein can be used to improve the muscular structure supporting facial skin, compared to tightening only the skin itself. The present methods can include tightening of muscles underlying skin in a target area and tightening of the skin itself. Exemplary temperature ranges for tightening of the muscles/skin, as noted above, can include delivering cooling to the target tissue from about −1° C. to about −10° C., or in some instances from about −25° C. to about −80° C.

In another method aspect, the invention provides a method for improving a cosmetic appearance of the patient. The patient has a skin surface with a tissue therebelow. The tissue has a mass, and the method comprises directing sufficient tissue-remodeling energy or cooling from a probe through the skin surface to induce a reduction in the mass of the tissue such that the cosmetic appearance of the skin surface is improved. Current methods can be used to reduce the mass of the skin itself, as wall as the mass of other target tissues, including for example a lesion (benign, malignant, etc.), scar, and the like (e.g., as further described below). Reduction of target tissue mass can include skin and/or target tissue of the face as well as other areas of the body.

In yet another method aspect, the invention provides a method for treating a patient. The patient has a skin surface and a muscle therebelow. The method comprises directing sufficient tissue remodeling energy or cooling below the skin surface so that contraction of the muscle is inhibited or a loss of elasticity is induced. Related methods may comprise applying chemicals, and/or a means of cutting-off the tissue's blood supply.

Along with directing of cooling to (for example) a component of the contractile chain of a muscle, embodiments of the invention may rely at least in part on any of a variety of forms of energy transmissions to these or other tissues so as to inhibit muscle contraction, decrease muscle (or other tissue) mass, and the like. Suitable energy forms that may be used in place of or in conjunction with cooling may include ultrasound energy, radio frequency electrosurgical energy, microwave energy, laser energy, electromagnetic or particle radiation, and the like. Optionally, any of these treatment modalities may be combined with the use of bioactive agents, chemicals, or varied method of cutting off the tissue's blood supply.

In another aspect, the invention provides a system for cosmetically reshaping an exposed skin surface of a patient. The system comprises a probe body having at least one cooling fluid supply path. At least one tissue-penetrating probe extends distally from the body. The at least one probe has a distal tissue-piercing end and is in thermal communication with the at least one cooling fluid supply path. A cooling fluid source is coupled to the at least one cooling fluid supply path so as to cool the at least one probe distally of the body. The cooling may remodel adjacent tissue when the at least one probe is inserted through the skin surface, and the remodeling may reshape the skin surface.

In many embodiments, a controller will be coupled to the cooling fluid path so as to control a treatment time and/or treatment temperature. The controller may have an input for identifying a desired duration of the remodeling, and the controller may determine a characteristic of the cooling in response to the desired duration.

In some embodiments, a cooling region of the probe or probes inserted through the skin surface may have a cooling region for selectively cooling the target tissue, with the cooling region optionally being separated from the proximal end of the insertable probe. For example, an insulated region may extend between the cooling region and a skin engaging surface of the probe body so as to inhibit injury along the skin surface. Materials and/or energy may be directed to tissues along the skin surface or any of a variety of other collateral tissues may be protected.

In another aspect, the invention provides a system for improving a cosmetic appearance of a patient. The patient has skin surface with a tissue therebelow. The tissue has a mass, and the system comprises a probe having a tissue engaging surface directing sufficient tissue-remodeling energy or cooling from the probe through the skin surface to induce a reduction in the mass of the tissue such that the cosmetic appearance of the skin surface is improved.

In yet another system aspect, the invention provides a system for treating a patient. The patient has a skin surface, and a muscle therebelow. The system comprises a transmission surface directing sufficient tissue remodeling energy or cooling below the skin surface so that contraction of the muscle is inhibited.

In another aspect, the present invention provides a method for treating a target tissue of a patient. The method includes inserting a needle probe distally to penetrate into the target tissue, and directing a cooling energy into the target tissue through the probe so as to remodel the target tissue and alter a surface of the patient's skin, thereby treating the target tissue of the patient.

Methods of the present invention can be directed to a variety of target tissues and are not limited to any particular tissue. Target tissues can typically include dermatological tissues and/or subcutaneous tissues. For example, a target tissue can include a patient's skin and/or tissue below the skin, or below an exterior surface of the skin. As set forth above, target tissues can include muscles or muscle containing tissues, nerves, blood vessels, as well as adipose tissues. Target tissues can also include various types of lesions, wounds, and the like, including, for example, various malignant (e.g., cancerous) or benign lesions, acne, warts, scar tissue, and the like.

As set forth above, embodiments of the present invention may be employed for a variety of conditions, including cosmetic conditions, for example, by inhibiting or ameliorating undesirable and/or unsightly effects that may be visible on the patient's skin (e.g., lines, wrinkles, cellulite dimples, lesions, scars, wounds, etc.) or on other surrounding or adjacent tissues. In one embodiment, directing of cooling energy according to methods of the present invention includes inhibiting contraction of a muscle of the target tissue. Delivery of cooling energy can have a variety of contraction inhibiting effects on the targeted muscle tissue and will not be limited to any particular mode or mechanism of action. In one embodiment, for example, delivery of cooling energy can denature proteins of the muscle or target tissue so as to inhibit contraction of the muscle. In another embodiment, the cooling is selected so as to modulate cellular signaling, such as calcium signaling, in the muscle of the target tissue. In yet another embodiment, the delivery of cooling energy can disrupt electrical signaling or affect a nerve's ability to stimulate muscle contraction or recruitment of a motor unit of the muscle of the target tissue, and can at least partially disrupt function of the muscle.

In another embodiment, the cooling can be selected so as to induce a reduction in tissue mass, for example, during or proximate to the time of energy delivery or after removal of the probe from the patient. Reduction of tissue mass can include mass reduction of any type of tissue amenable to treatment according to the inventive methods described herein, including, for example, adipose tissue (e.g., macrosculpting/microsulpting fat), muscle tissue, skin tissue, tissue of a wound or lesion (e.g., benign lesion, malignant lesion, wart, scar tissue, acne, etc.), and the like. In yet another embodiment, delivery of the cooling energy can promote healing of the target tissue (e.g., lesion, wound, etc.).

In yet another aspect of the present invention, a method for treating a target tissue of a patient is provided. The method includes inserting a needle probe distally to penetrate into a target tissue of the patient, and directing a cooling energy into the target tissue through the probe so as to inhibit contraction of a muscle of the target tissue and remodel the target tissue. In some instances, delivery of the cooling energy to the target tissue can be accomplished using a non-penetrating probe. Thus, in another aspect, a method of treating a target tissue of a patient is provided, the method including positioning a non-penetrating probe in contact with a skin surface of the target tissue, and directing a cooling energy through the probe and into the target tissue so as to remodel the target tissue. Target tissues can include, for example, a lesion, such as an acne lesion.

In another aspect, a system for treating a target tissue of a patient is provided. The system includes a body comprising at least one cooling fluid supply path; at least one needle probe having a proximal portion, a distal portion, and a lumen therebetween, the at least one needle probe extending distally from the body and insertable into a target tissue of a patient; a cooling fluid source coupleable to the fluid supply path to direct cooling fluid flow into the needle probe lumen; and a controller coupled to the cooling fluid supply path, the controller comprising instruction that, if executed, cause the system to direct a cooling energy into the target tissue through the needle probe, the cooling energy selected to remodel the target tissue and alter a surface of the patient's skin or provide a therapeutic effect.

BRIEF DESCRIPTION OF THE DRAWINGS

FIGS. 2 and 2A-2L illustrates target tissues for treatment in some embodiments of the present invention, along with associated lines or wrinkles and treatment patterns.

FIG. 15B illustrates a "ratchet action" movement or a sliding filament movement illustration of muscle contraction.

DETAILED DESCRIPTION OF THE INVENTION

Figure 1A:
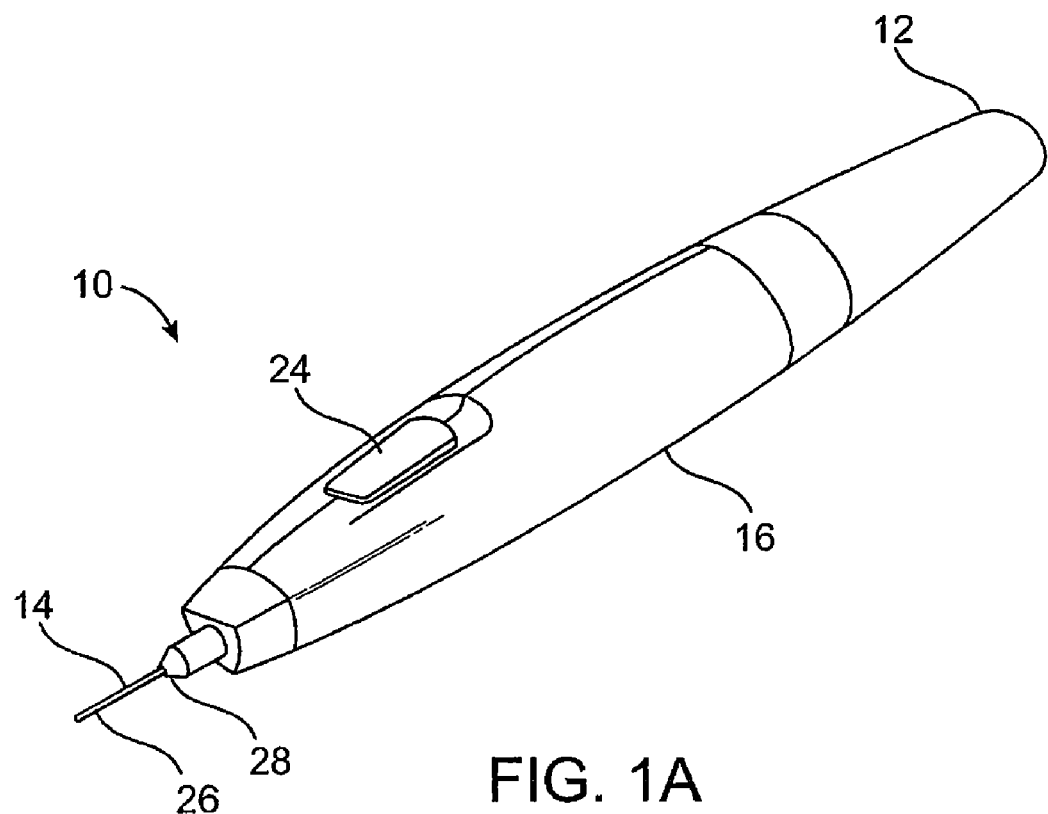
FIG. 1A is a perspective view of a self-contained subdermal cryogenic remodeling probe and system, according to an embodiment of the invention.

The present invention provides improved medical devices, system, and methods. Embodiments of the invention will facilitate remodeling of tissues disposed below the skin, often so as to alter a shape of the overlying skin surface, in many cases while inhibiting or avoiding collateral injury to the skin and associated skin scarring, discoloration, and the like. Tissues amenable to the inventive methods include skin tissues as well as tissues disposed on or below the skin and may provide a cosmetic or therapeutic effect, or both.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 1° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., optionally so as to provide a permanent treatment that limits or avoids inflammation and mobilization of skeletal muscle satellite repair cells. Apoptosis also may be induced using treatment temperatures below about −15° C., including temperatures from about −1° C. to about −20° C. Hence, the duration of the treatment efficacy of such subdermal cryogenic treatments may be selected and controlled, with colder temperatures, longer treatment times, and/or larger volumes or selected patterns of target tissue determining the longevity of the treatment.

In addition to cosmetic treatments of lines, wrinkles, and the like, embodiments of the invention may also find applications for treatments of subdermal adipose tissues. Embodiments of the invention may also find applications for alleviation of pain, including those associated with muscle spasms. Still further embodiments may rely on application of energy (with or without cooling) for remodeling of target tissues and producing a desired cosmetic effect, with the energy optionally comprising focused or unfocused ultrasound energy, radio frequency energy, laser energy microwave energy, other electromagnetic or particle radiation, alternative methods of applying heat, chemicals, vascular embolization, and the like. Hence, a variety of embodiments may be provided. In one embodiment, for example, delivery of energy, such as radio frequency energy, can be used to target and disable muscle tissue of the target tissue as opposed to targeting nerve ablation to block competition.

Figure 1B:
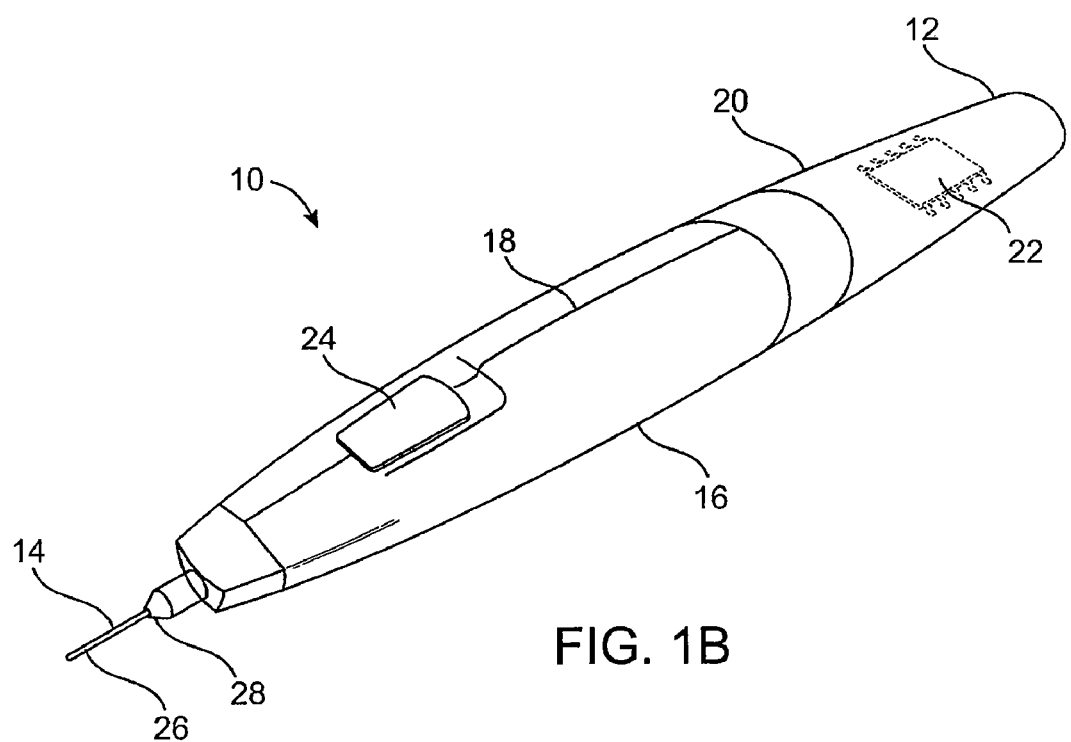
FIG. 1B is a partially transparent perspective view of the self-contained probe of FIG. 1A, showing internal components of the cryogenic remodeling system.
Figure 1C:
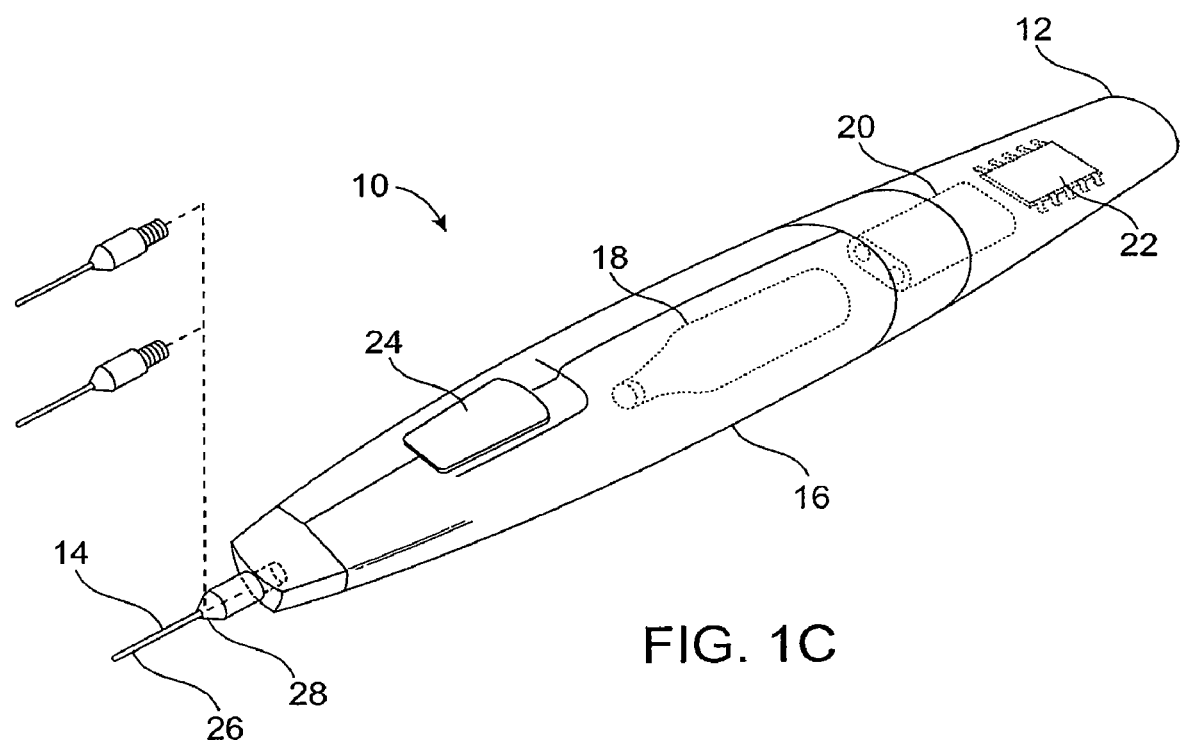
FIG. 1C is a partially transparent perspective view of the self-contained probe of FIG. 1A, showing internal components of the cryogenic remodeling system and schematically illustrating replacement treatment needles for use with the disposable probe.

Referring now to FIGS. 1A, 1B, and 1C a system for subdermal cryogenic remodeling here comprises a self-contained probe handpiece generally having a proximal end 12 and a distal end 14. A handpiece housing 16 has a size and shape suitable for supporting in a hand of a surgeon or other system operator. As can be seen most clearly in FIG. 1B, a cryogenic cooling fluid supply 18 and electrical power source 20 are found within housing 16, along with a circuit 22 having a processor for controlling cooling applied by self-contained system 10 in response to actuation of an input 24.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Needles of various sizes can be included in the present invention and can include needles smaller than 20 g needles, as well as embodiments with needles sized from 14 g to 32 g. Probe 26 may have an axial length between distal end 14 of housing 16 and the distal end of the needle of between about ½ mm and 5 cm, preferably having a length from about 1 mm to about 3 mm, and from about 1 cm to about 3 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Additionally, while needles are generally illustrated herein as being straight or substantially linear, needles suitable for use in the present invention can include a variety of shapes and configurations. For example, needles can be curved or comprise a curved portion, including pre-bent or curve-shaped needles, and the like. Also, while a needle or probe 26 will generally extend distally from the distal end 14 of the housing, the positioning of the probe is not limited to any particular orientation and can, for example, extend substantially along a long axis of the housing 16, or the probe 26 can be at an angle relative to the long axis. Particular shape and/or configuration or orientation of the probe 26 may depend at least partially on the intended use of the device, as certain probe shapes, configurations, and/or orientations may be desired for particular treatments or probe positioning within a target tissue.

Addressing some of the components within housing 16, the exemplary cooling fluid supply 18 comprises a cartridge containing a liquid under pressure, with the liquid preferably having a boiling temperature of the less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 18 and probe 26, or along the cooling fluid path after the probe so as to limit the temperature, time, rate of temperature change, or other cooling characteristics. The valve will often be powered electrically via power source 20, per the direction of processor 22. The exemplary power source 20 comprises a rechargeable or single-use battery.

The exemplary cooling fluid supply 18 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide. The quantity of cooling fluid contained by cartridge 18 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid. Other embodiments can include liquid $N_2O$ cartridge in a quantity less than about 7 g, including embodiments designed for a smaller limited amount of use or even single use.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like)

may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

It will be noted that systems and devices of the present invention can make use of a variety of power sources including, for example, an on-board power sources, such as a battery that can provide for a more portable and/or maneuverable, as well as self-contained, system or device. In one embodiment, for example, a power source 20 (e.g., battery) can be positioned in and/or affixed to the handpiece housing 16 or otherwise coupled with the housing 16 in a manner such that the probe device, including the needle probe 26, battery or power source 20, as well as other components, can be manipulated and positioned my manipulation of the handpiece housing 16.

Figure 2:
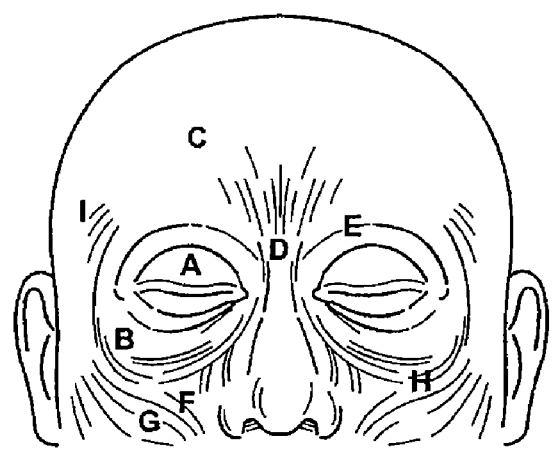
Figure 2M:
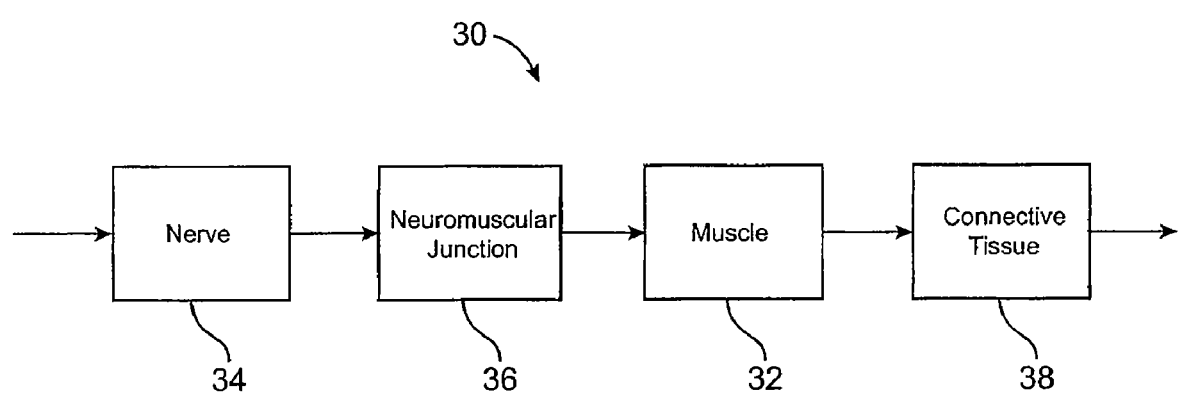
FIG. 2M is a functional block diagram graphically illustrating tissue components included in a contractile chain.
Figure 2A:
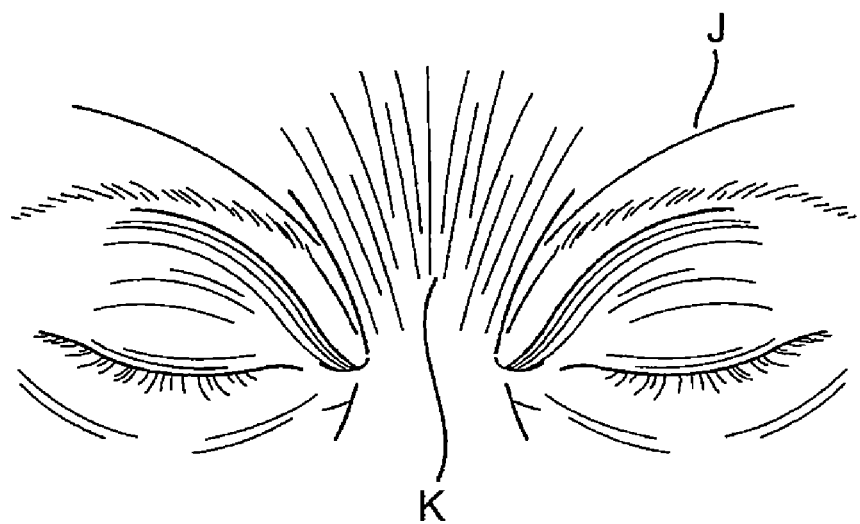
Figure 2B:

Referring now to FIGS. 2 through 2M, subdermal cryogenic remodeling of tissues for alleviation of lines and wrinkles will find particular applications for skin surface regions of the face and neck, with procedures optionally being performed so as to alter contractile function of muscles A-I in the upper one-third of the face as shown in FIG. 2. Treatments may be performed so as to alleviate frown lines, lines or wrinkles between the eyes, crow's feet, horizontal lines in the forehead, neck, wrinkles around the mouth, chin, and the like. Many of these cosmetic defects may be treated by targeting and/or inactivating tissues such as the corrugator and/or procerus muscles. More specifically, as seen in FIGS. 2A and 2B, movement of the facial muscles can cause the skin to crease, for example, with contraction of corrugator muscle J and/or procerus muscle K leading to creases between the brows L, which may be clinically referred to as glabellar lines. Additional treatment locations, muscles M-Q whose contractile function may be targeted, related lines or wrinkles, and treatment patterns R are illustrated in FIGS. 2C-2L.

Regarding the specific muscles and tissue structures identified in FIG. 2, treatments may be directed towards one or more of levator palpebrae superioris A, orbicularis oculi B, frontalis C, levator labii D, corrugator E, zygomaticus minor F, zygomaticus major G, buccinator H, and/or temporalis I. Treatments targeting contraction of oticularis M of FIG. 2C may help decrease crow's feet wrinkles of FIG. 2H, optionally using a treatment pattern R. Treatments altering the function of Frontalis N of FIG. 2D may alleviate the wrinkles of FIG. 2I, while altering functioning of Orbicularis O of FIG. 2E may alleviate the wrinkles shown in FIG. 2J. Wrinkles of the chin as shown in FIG. 2K may be mitigated by treatment of Mentalis P and neck wrinkles such as those of FIG. 2L may be improved by treatments of platysma Q, as seen in FIG. 2G. Treatment patterns R for improvement of these and other cosmetic defects may correspond to or be derived from known treatments (such as patterns for injections of BOTOX® or the like), may be determined by anatomical analysis using the desired physiological effects, by animal or clinical studies, or the like.

Target muscles for contraction inhibition so as to alleviate wrinkles and the like may often include the glabellar and procerus complex including, but not limited to, the corrugator procerus, orbicularis oculi, depressor, supercilli, and frontalis. Other muscle groups of the facial region may also be contraction-inhibited, such as the nasalis, orbicularis oris, buccinator, depressor anguli oris, quadratus labii superioris and inferioris, zygomaticus, maxillae, platysma, and mentalis. Contraction of these and/or other muscles may be inhibited by targeting associated nerve tissues, connective tissues, nerve/muscle interface, blood supply, and/or at least a portion of tissues of one or more of these muscles themselves. Preferred wrinkle alleviation treatments may alter functioning of muscles including one or more of, but not limited to, frontalis pars medialis, frontalis pars lateralis, corrugator supercilii, procerus, depressor supercilii, levator palpebrae superioris, orbicularis oculi pars orbitalis, orbicularis oculi pars palpebralis, levator labii superioris alaquae nasi, levator labii superioris, zygomaticus minor, zygomaticus major, levator anguli oris (a.k.a. caninus), buccinator, depressor anguli oris (a.k.a. triangularis), depressor labii inferioris, mentalis, incisivii labii superioris, incisivii labii inferioris, risorius, platysma, orbicularis oris, masseter, temporalis, internal pterygoid, digastric, nasalis, maxillae, quadratus labii superioris and inferioris.

In many embodiments, remodeling a tissue included in a contractile function chain 30 will effect a desired change in a composition of the treated tissue and/or a change in its behavior which is sufficient to mitigate wrinkles of the skin associated with contraction of a muscle 32, as illustrated in FIG. 2M. While this may involve a treatment of the tissues of muscle 32 directly, treatments may also target nerve tissues 34, neuromuscular junction tissues 36, connective tissues 38, and the like. Still further tissues may directly receive the treatment, for example, with treatments being directed to tissues of selected blood vessels so as to induce hypoxia in muscle 32 or the like. Regardless of the specific component of contractile chain 30 which is treated, the treatment will preferably inhibit contraction of the muscle 32 which would otherwise form wrinkles or lines in the exposed skin surface overlying that muscle.

A variety of specific tissue remodeling treatments mechanisms targeting of one or more components of contractile chain 30 may be employed so as to inhibit lines or wrinkles. For example, ablation of muscle cells/tissues, or the associated nerves (optionally being a component thereof integral to nerve function such as a myelin sheath or the like), or the nerve endings or neuromuscular junction (which generally forms the interface between the nerves and the muscles) may be sufficient to inhibit muscular contraction. Such ablation may result in a short-term, long-term or permanent inactivation of the muscle. Other long-lasting or permanent treatments may involve inducing apoptosis, typically at temperatures which are not as severe as ablation temperatures, but which remodel the tissue behavior with long term changes in the cellular life and/or proliferation cycles. Specific remodeling mechanisms so as to change the function of the muscle in a desired way or for a desired time may be induced by appropriate therapeutic dosages of the treatment modalities described herein, for example so as to induce cell death (apoptotic or necrotic), embolization of blood supply, or the like. Alternative remodeling mechanisms which may be shorter in effect may include stunning of one or more component of contractile chain 30, inactivation of one or more component, or the like. Remodeling treatments which effectively block the release of or response to chemicals (such as but not limited to acetylcholine) along the contractile chain 30 may be sufficient to inhibit muscular contraction in response to signals transmitted along the neural pathways, either temporarily or permanently, and may also be employed.

Muscular movement is generally controlled by stimulation of a nerve. The motor unit of the neuromuscular system contains three components: motor neuron (spine), axon (spine to motor endplate), and innervated muscle fibers (endplate to muscle). Treatments directed to one or more of these tissues may be employed.

When treatments are intended to inhibit muscle contraction, the treatment may be determined at least in part by the type of muscle being treated (skeletal (striated) or smooth (not striated)). For example, skeletal muscle may have muscle fibers that are innervated by motor neuron, with a single neuromuscular junction lying along a midpoint of muscle fibers, and a single muscle fiber within a motor unit supplied by a single motor neuron and its axon. Each muscle receives one or more nerves of supply, and the nerve generally enters deep into the muscle surface near its origin where the muscle is relatively immobile. Blood vessels typically accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle—epimysium, perimysium, endomysium—each terminating in several branches joining a muscle fiber at the motor endplate. Remodeling of one or more of these tissues may be sufficient to temporarily or permanently inhibit muscle contraction.

Embodiments of the invention may interrupt or disable nerve impulses by disrupting conductivity by eliminating or decreasing charge differences across plasma membranes, either mechanically or chemically; by destroying Schwann cells that insulate the axonal processes speeding up impulse conduction; and/or by repeated injury/healing cycles timed to limited capacity for neuron regeneration.

Immobilization of muscle by disabling any one or a specified combination of components of the connective tissue matrix, either temporarily or permanently, may also be employed. Treatments targeting connective tissues, such as the fibroblasts, myofibroblasts (which may be responsible for contractility of granulation tissue in healing), collagen, reticulin, elastin, or the like of aponeurotic or tendinous attachment of muscles to bone, fascia, ligaments, or the like may also be advantageous, and the remodeling form and/or treatment dosage may be selected in response to the condition being treated (for example, when primarily treating cellulite dimples rather than primarily treating contraction-induced lines or wrinkles). Treatments of the superficial fascia just beneath the skin may also be employed. To achieve a loss of elasticity in fibrous connective tissue during treatment of cellulite, temperature may be varied to achieve temporary or permanent changes to the morphology of the collagen and elastin matrix contained within that tissue.

Along with treating of the target tissue using probe 26, it will often be desirable to inhibit injury to collateral tissues underlying and adjacent to the target tissues, and particularly to the tissues along the skin surface overlying the target tissues. Injury to any desired tissue (blood vessels, nerves, etc.) may be inhibited, particularly if that tissue is determined to not be targeted in a particular therapy. As illustrated in FIGS. 1A and 1B, a distally oriented applicator 28 adjacent in the distal end 14 of housing 16 may apply energy and/or a material along the skin surface adjacent probe 26 so as to protect the surface tissues from the treatment temperatures. Applicator 28 may, for example, be oriented to engage tissues along the skin surface when the probe 26 is inserted therethrough, the applicator heating the skin surface to prevent injury from the cooling probe. Heating may be provided by a resistive heater or the like, and heat may be transferred to the tissue-penetrating probe body from applicator 28 so as to inhibit injury from the proximal portion of the probe to the adjacent skin tissues. Other embodiments may apply a heated cryoprotectant material above or below the skin surface.

So as to protect adjacent tissues from injury, it may also be advantageous to meter the cooling fluid (such as the liquid $N_2O$) in thermal communication with probe 26 so as to minimize the overflow during treatment times. The amount of liquid $N_2O$ or mass flow rate flowing into a needle probe may be a function of pressure of fluid from fluid source 18, a fluid tube inlet diameter, an internal pressure within the needle, and the quality of the $N_2O$. The amount of liquid $N_2O$ desired to operate a needle probe may be a function on the desired temperature difference between the needle and tissue, which may change over time. Outgoing gas temperatures from the needle probe may change the quality of the incoming $N_2O$ flowing into the needle. Hence, as a result of the dynamic flow requirements, it may be difficult to precisely meter only the amount of desired $N_2O$.

Figure 3:
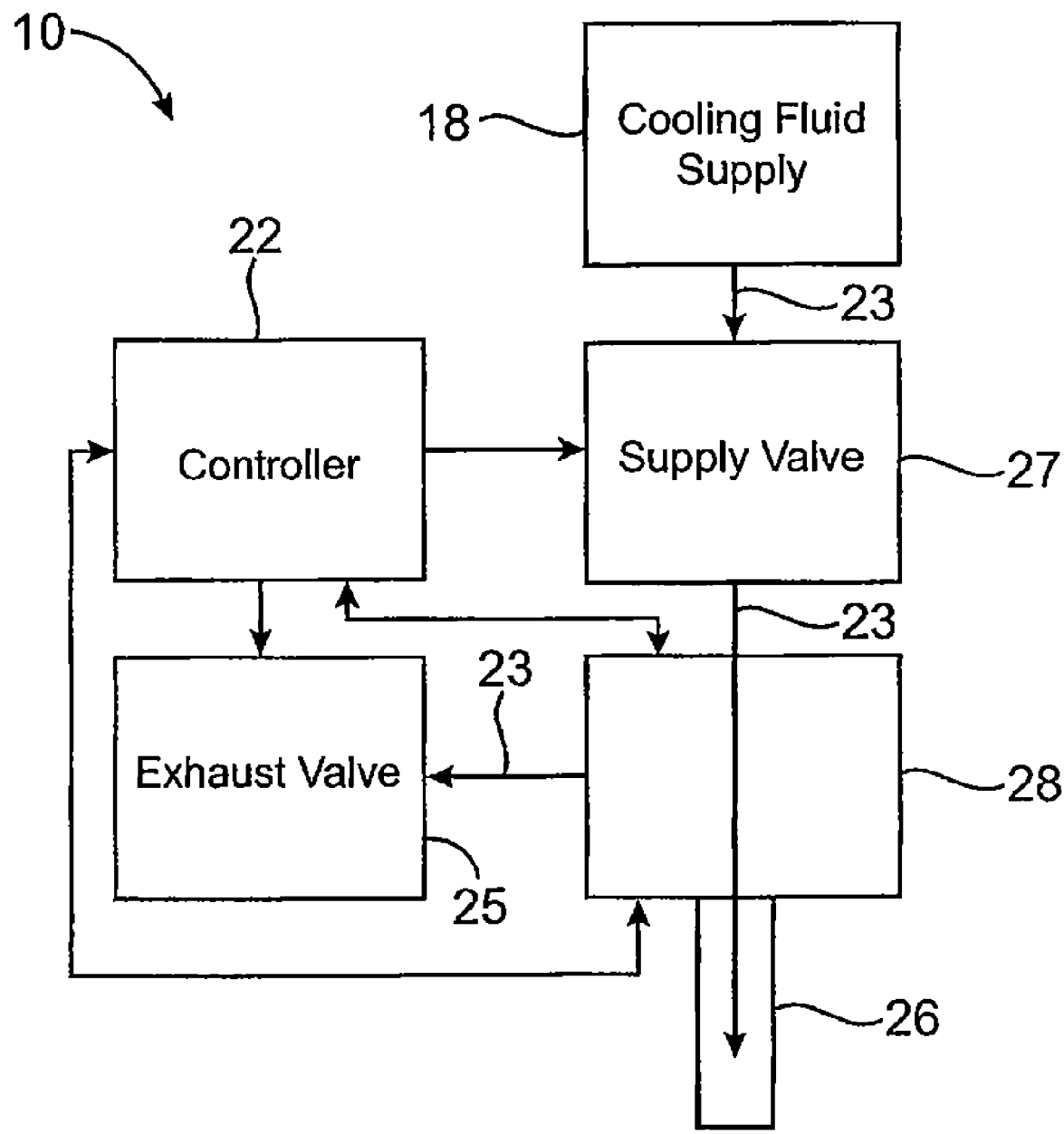
FIG. 3 is a block diagram schematically illustrating functional components of the self-contained probe of FIG. 1A.

Referring now to FIG. 3, a cooling fluid path 23 generally extends from fluid supply 18 to tissue penetrating probe 26, and from the probe to an exhaust (often via exhaust valve 25). A supply valve 27 will often be disposed along fluid path 23 to help control any cooling fluid overflow condition, with the supply valve typically comprising a solenoid or other valve controlled by signals from controller circuit 22. Controller 22 may also provide control signals to exhaust valve 25 in response to temperature or cooling fluid pressure signals, typically so as to control a temperature of probe 26 and/or a pressure of the cooling fluid therein (or adjacent thereto). Similarly, controller 28 may also control operation of applicator 28, such as by varying electrical energy supplied to a resistive heater in response to a temperature of a temperature-engaging surface of the probe or a temperature of the engaged skin or the like. Controller 22 may transmit signals for other applicators so as to control a flow of fluid from the applicator, for example, by energizing a pump, actuating a valve, or the like.

To control any overflow of cooling fluid into or through probe 26, supply valve 27 along cooling fluid path 23 between fluid supply 18 and the probe 26 may be pulsed so as to allow sufficient flow during different portions of the treatment. Pulsing of the cooling fluid in a device of system of the invention can also be accomplished, for example, so as to preserve cooling fluid or make more efficient use of the cooling fluid during treatment or use of the device. Pulsing of cooling fluid can be accomplished in a manner similar to pulsing of cooling fluids as is known in other contexts or methods making use of cryogenic techniques.

TABLE 1

EXAMPLE OF A 20 SECOND TREATMENT

| Time | Valve Position | Duration |
| --- | --- | --- |
| 0-5 seconds | Open | 5 seconds |
| 5-7 | Closed | 2 |
| 7-11 | Open | 4 |
| 11-13 | Closed | 2 |
| 13-16 | Open | 3 |
| 16-18 | Closed | 2 |
| 18-20 | Open | 2 |

Table 1 shows an exemplary operation timing for valve 27. During the portions of the treatment when the valve is closed, refrigerant may continue to flow into probe 26, although at a reduced pressure and correspondingly reduced flow rate. The pressure may decay by a rate determined by the volume of the refrigerant fluid path coupling valve 27 to probe 26 (and/or to tube 58 in FIG. 5B). As shown in this example, the proportion of valve open or flow time may be reduced in later stages of the treatment (for example, after more than about 5 seconds of treatment) to match the smaller desired flows. Different probes or probe arrays having different numbers of probes, different lengths, and the like may be mechanically or electronically coded to provide signals to controller 22 so that the controller delivers appropriate on/off (or other modulated) valve timing. Each individual probe may be experimentally characterized to determine appropriate valve timing or other modulation so as limit or avoid refrigerant overflow conditions.

Figure 3A:
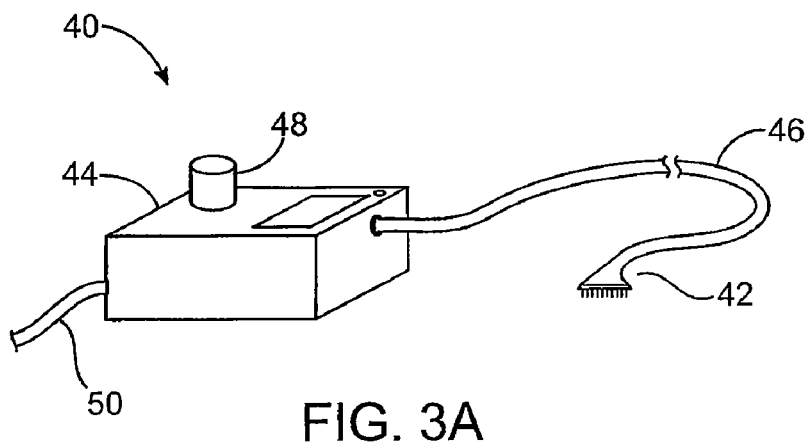
FIG. 3A is a perspective view schematically illustrating another embodiment of a subdermal cryogenic remodeling system having a distal probe handpiece coupled to a proximal housing by a flexible body.

Referring now to FIG. 3A, an alternative subdermal cryogenic remodeling system 40 includes a distal probe handpiece 42 coupled to a proximal controller housing 44 by a flexible body 46. Housing 44 includes a replaceable cooling fluid cartridge 48, with the exemplary cartridge again containing liquid $N_2O$ and a connector for electrical power 50. Housing 44 also includes or contains a user interface for accepting inputs from the system user into a processor contained within the housing, and for outputting parameters regarding the state of the system, the progress of treatment, tissue and/or treatment parameters, and the like.

Figure 3B:
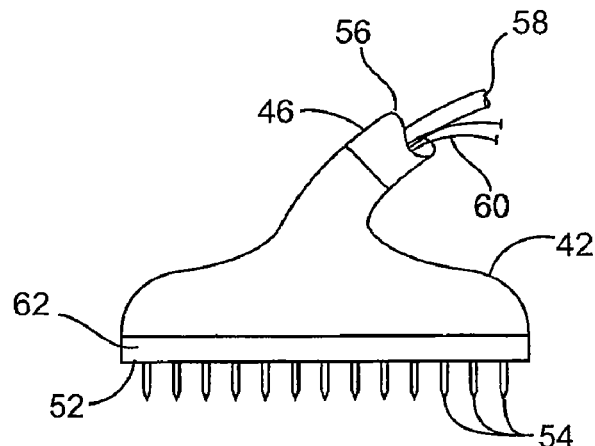
FIG. 3B is a side view schematically illustrating the distal handpiece of the system of FIG. 3A, showing a probe body with a plurality of tissue-penetrating probes extending therefrom.

Referring now to FIGS. 3A and 3B, probe handpiece 42 generally extends distally from flexible probe body 46 to a distal tissue engaging surface 52. A plurality of tissue-penetrating needle probes 54 extend distally from tissue engaging surface 52, with the needle probes being cooled by cryogenic cooling fluid from fluid source 48. Flexible body 46 may include a lumen 56 through which the vaporized cryogenic cooling fluid returns from thermal contact with probes 54 to housing 44, with the housing 44, handpiece 42, or flexible probe body 46 including a valve for regulating pressure of the exhaust gases so as to control a treatment temperature under the direction of the processor within the housing. A cooling fluid supply lumen 58 may also be included within flexible body 46 for transmitting the liquid cooling fluid to probes 54. Electrical power for handpiece 42 may be provided from housing 44 by electrical conductors 60.

In the embodiment of FIG. 3B, handpiece 42 includes an applicator in the form of a heated pad 62, the distal surface of the heating pad comprising the tissue engaging surface 52. In general, the temperature of the skin engaging surface of the probe may be between about 37° C. and about 90° C., with warmed probe tissue engaging surfaces having a temperature from about 45° C. to about 90° C. before skin contact, depending of the physical properties of the probe surface, so that the skin has a temperature from about 37° C. to about 45° C. during treatment. Probe surfaces formed on thermally conductive materials (for example, metals such as copper, aluminum, or the like) may be heated so as to have temperatures closer to 45° C. prior to contact with the skin, while non-heat conductive materials (often including polymers such as a silicone or a PTFE such as a Teflon™ material) may be heated to have temperatures closer to 90° C. before contact. Other factors which may influence the desired probe skin engaging surface temperature before skin contact include the mass of the underlying probe structure, the location of the heater, and the like. Independent of the initial probe temperature at contact, the maximum desired temperature that the skin reaches may be about 45° C. To protect the skin and/or surrounding tissue, the probes described here may be provided with applicators which apply heat energy, materials, or the like to inhibit injury along the skin surface or other tissue not targeted by a particular therapeutic treatment. In another embodiment, the heating pad may not necessarily be specifically heated, but can act sufficiently as a heat sink or a protective insulating sleeve.

The application of energy can heat collateral tissues near tissues targeted for application of cooling-based remodeling, such as to control temperatures at the inner and/or outer surfaces of the skin, in the surrounding tissues, or the like. This may be achieved with energy sources and/or by applying temperature managed fluid. In FIG. 3B, the exemplary applicator comprises, for example, heating pad 62 of stainless steel or the like. Heating of the applicator may be provided by a resistive heater structure powered by conductors 60 under the direction of the processor circuitry contained within controller housing 44.

Along with circuitry for controlling the heater of the tissue engaging probe surface, the processor circuitry within controller housing 44 will provide on/off or metered flow control for the $N_2O$ (as well as pressure regulation), a timer for applying and/or varying heating, cooling, the application of cryoprotectants or other materials, or the like. A wide variety of pre-cooling, during-cooling, and/or post-cooling collateral tissue inhibiting treatment regimens may be employed so as to allow the target tissues to be cooled to the desired treatment temperatures for the desired treatment times with appropriate rates of change in the temperature to provide the desired remodeling effect, while collateral tissues along the skin surface or the like are maintained at injury inhibiting temperatures.

Figure 3C:
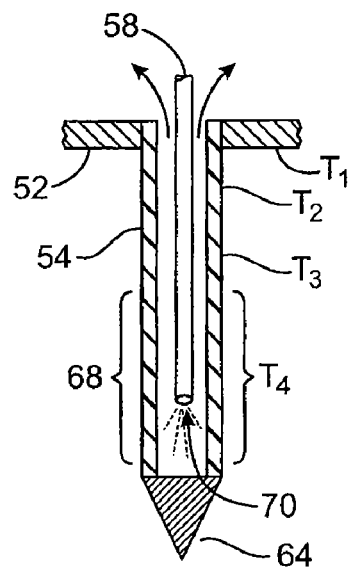
FIG. 3C is a cross-sectional view showing the structure of the tissue-penetrating probes of the probe body of FIG. 3B.

Referring now to FIGS. 3B and 3C, the cooling and structure of tissue-penetrating probes 54 can be seen in more detail. Each probe again comprises a 30 g 0.012 inch outer diameter tube or needle having a sharpened distal end 64. Additional needle sizes can also be employed, as discussed further herein. A temperature along the skin-engaging surface 52 (and hence adjacent the proximal end of tissue-penetrating probe 54) $T_1$ may be warmer than skin temperature, typically being warmer than 37°, and in the exemplary embodiment being about 50° C. A distal portion of the tissue-penetrating probe 54 for engaging a target tissue will have a temperature $T_4$ that is generally less than 10° C., often being 0° C. or less, and in many embodiments being −5° C. or less, in some embodiments being −15° C. or less, or even −25° C. or less so as to provide a sufficient tissue volume in the desired tissue temperature range. The exemplary penetrating needle 54 shown in FIG. 3C may have a distal portion 68 with a length of over about 1 mm, optionally being about 3 mm in length, and may be cooled to provide a probe outer surface treatment temperature $T_4$ of about −40° C. In some embodiments the treatment temperature can be cooler than about −40° C., including, for example, between about −40° C. and about −70° C.

A portion of the cooling fluid directed to handpiece 42 is transmitted along a cooling fluid lumen 58 within the handpiece (from a manifold or the like, or optionally with each tissue-penetrating probe having an associated lumen extending through flexible body 46), with at least a portion of the cooling fluid flowing as a liquid from a cooling fluid inlet 70 into the interior of tissue-penetrating probe 54. The cooling fluid vaporizes within probe 54, and the exhaust gases are vented proximally into an interior of handpiece 42, then through lumen 56 of flexible body 46.

Referring still to FIG. 3C, distal portion 68 of probe 54 will generally contain a mixture of cooling fluid in its liquid form with cooling fluid in its gaseous form. As the vaporization or boiling temperature of a fluid generally varies with pressure, if the pressure within distal portion 68 is relatively constant, the probe surface treatment temperature $T_4$ along distal portion 68 will be relatively constant and can be controlled by varying the pressure within probe 54 and/or handpiece 42.

The outer probe surface temperatures $T_2$, $T_3$ between distal portion 68 and skin engaging surface 52 will typically be somewhat warmer than the target tissue probe treatment temperature $T_4$, particularly when the skin engaging surface 52 is heated. As the mix of liquid and gas cooling fluid flows proximally within tissue-penetrating probe 54 and, the liquid may eventually fully vaporize allowing the gas to increase in temperature. Hence, the outer probe surface may warm gradually as you move proximally from the distal portion 68. Even where the liquid is not fully vaporized, heat may be transmitted from heated pad 62 distally along the probe body. In the exemplary embodiment, the intermediate temperature $T_2$ may be about 0° C., with the temperature $T_3$ being about −20° C.

Figure 4A:
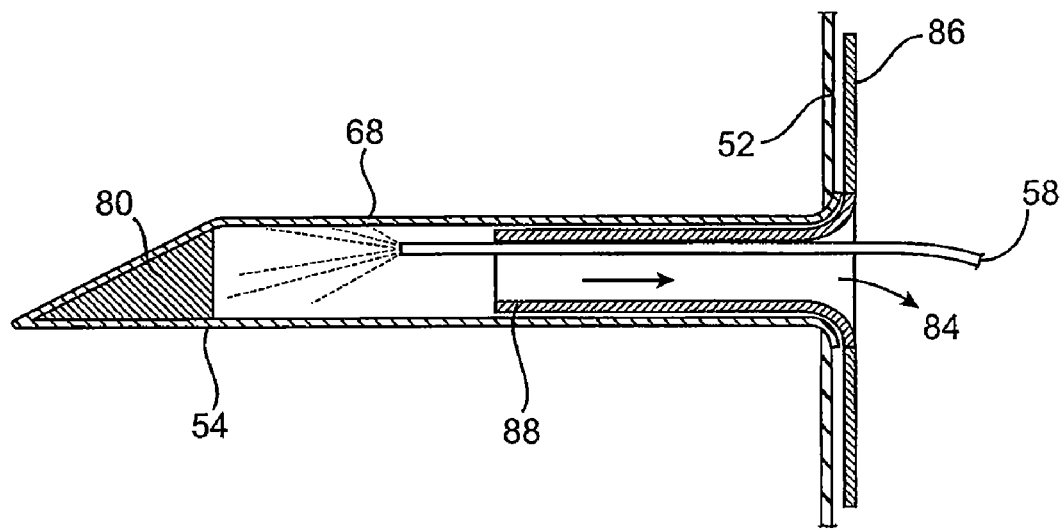
FIG. 4A is a cross-sectional view of an alternative tissue-penetrating probe having insulation along a proximal portion of the probe so as to inhibit cooling adjacent in the probe body.
Figure 4B:
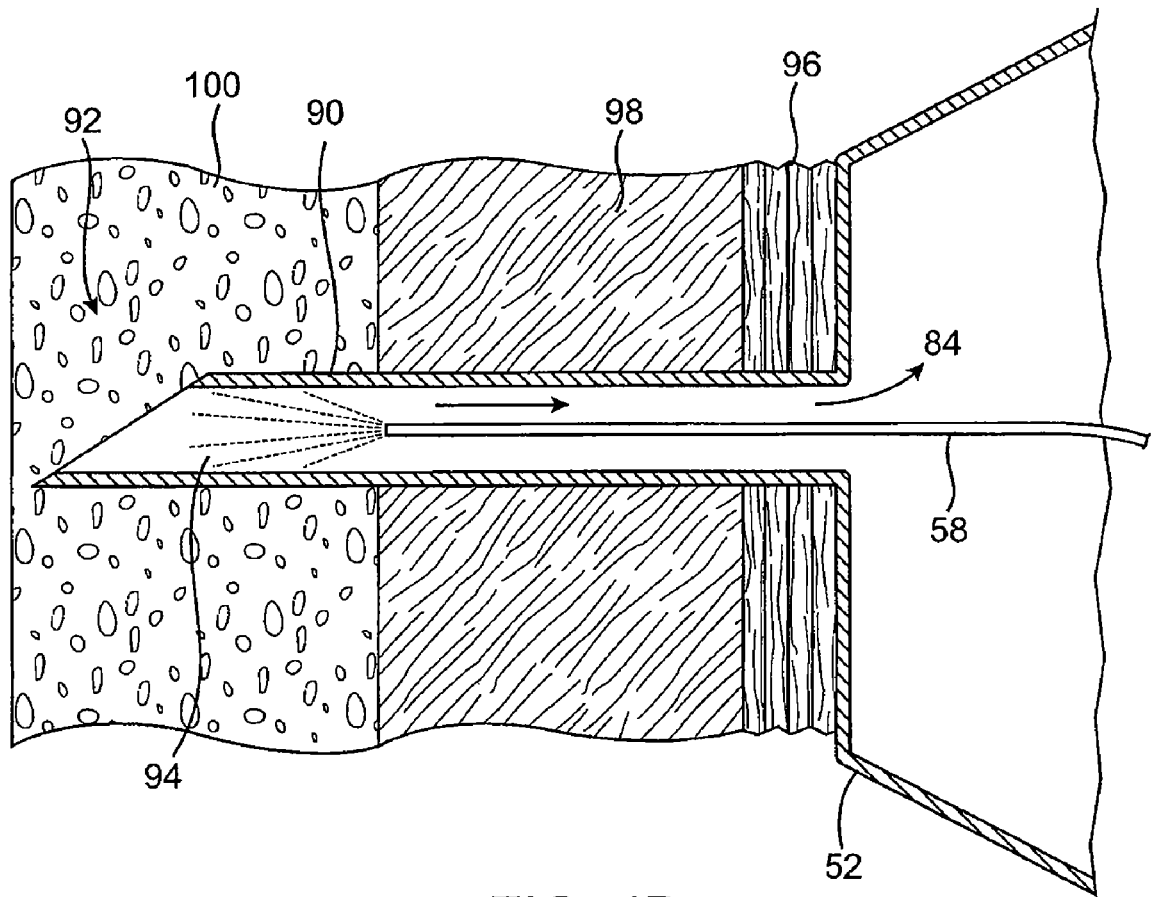
FIG. 4B is a cross-sectional view showing a still further alternative tissue-penetrating cryogenic probe having an open distal end, along with a method for its use.

Referring now to FIGS. 4A and 4B alternative mechanisms may also be provided to inhibit injury along the skin surface, including thermally insulating at least a portion of the tissue-penetrating probe or skin-engaging surface of the probe handpiece. Tissue-penetrating probe 54 here again comprises a 30 g stainless steel tube having an outer diameter of about 0.012 inches and an inner diameter of about 0.006 inches, with a closed distal end 80. It will be recognized that exemplary needle dimensions are illustrative, and that additional needle sizes and dimensions will be suitable for use according to the present invention, as recited above. Liquid $N_2O$ is again introduced through cooling fluid supply lumen 58, with vaporized gasses $N_2O$ 84 being exhausted proximally through the inner lumen of tissue-penetrating probe 54. Optionally, closed end 80 may limit the advance of cooling fluid within tissue-penetrating probe 54 so as to inhibit cooling of collateral tissues disposed distally of the target tissues, with the closed distal end optionally having a resistive heater, an insulating material, a tissue heating electrode, a cryoprotectant delivering port, or some other distal tissue protection applicator.

In the embodiment of FIG. 4A, insulation 86 is provided between the cooling fluid flowing within the probe handpiece and the skin engaging surface 52 to protect the epidermis from thermal coupling with any overflow liquid $N_2O$ or the like. Additionally, an insulation layer or sleeve 88 disposed between an outer surface of probe 54 and the cooling fluid within probe 54 limits thermal cooling by the cooling fluid proximally of the distal target tissue-engaging portion 68.

Optionally, direct cooling of the target tissue through contact between the cooling fluid and cooling tissue may be provided, as illustrated in FIG. 4B. In this embodiment, a probe 90 has an open end 92. Liquid $N_2O$ 94 (or some other cryogenic cooling fluid) is directed from cooling fluid lumen 58 toward open end 92, with vaporized exhaust gases 84 again returning proximally.

When probe 90 is inserted through the layers of the epidermis 96 and dermis 98 so that the distal portion of the probe is within a target tissue 100, the skin-engaging surface 52 of the probe handpiece is pushed firmly against the skin, thereby providing pressure to the dermal layers in the target tissue. The target tissue 100 partially invaginates in the needle lumen of probe 90, blocking the distal end closed. The combined compression of the target tissue and invagination contain the nitrous oxide $N_2O$ (or other cooling fluid) within the needle probe 90.

Figure 5A:
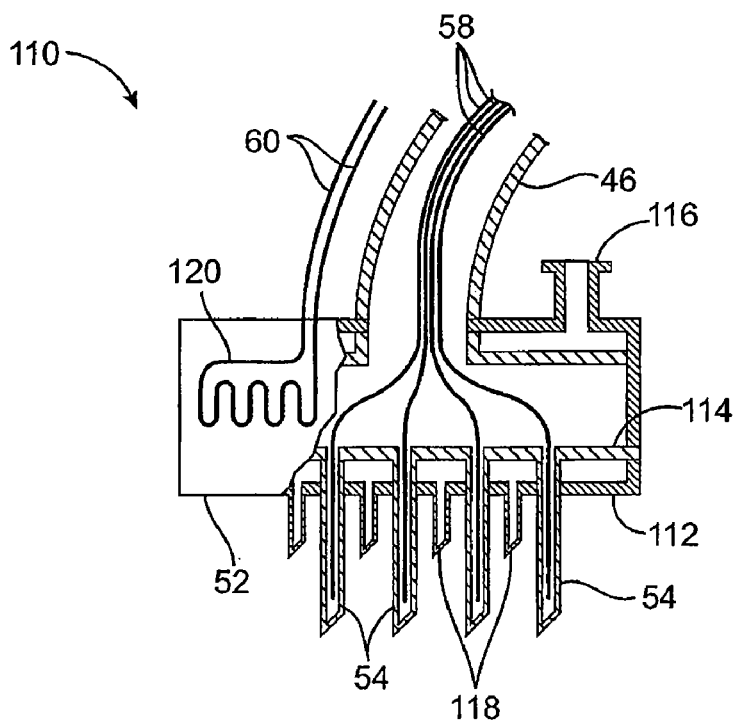
FIGS. 5A and 5B schematically illustrate cross-sectional views of an alternative treatment probe handpiece having a plurality of tissue-penetrating cooling probes, and also having an applicator for applying energy and/or an injectable material to inhibit cooling injury between the target tissues and the skin surface.
Figure 5B:
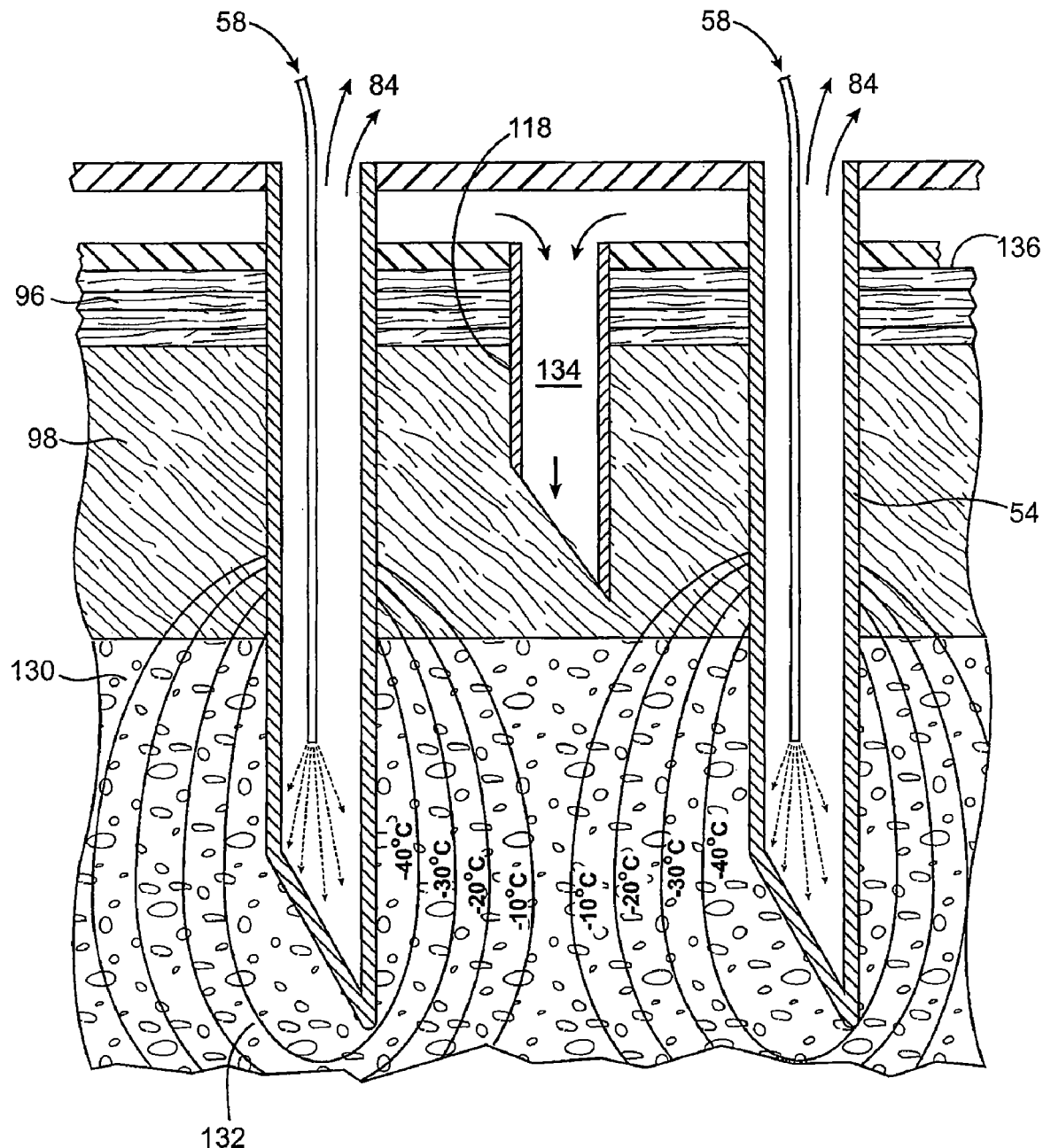

Referring now to FIGS. 5A and 5B, alternative probe handpiece 110 has an applicator 112 that applies both heating and a cryoprotectant compound to the tissues disposed between the skin surface and the target tissues to inhibit collateral tissue damage.

The application of one or more cryoprotectant compounds (such as dimethyl sulfoxide, DMSO, and/or the like) to the inner and/or outer surface of the skin, into the collateral tissue, or the like, with or without heating of the compounds, may inhibit collateral tissue damage. Probe handpiece 110 may also be used to inject warmed biocompatible fluids such as saline into the dermal layers above the target tissue so as to inhibit collateral tissue damage. DMSO or other cryoprotectants or biocompatible solvents may be applied to the epidermis and/or dermis before or during treatment. A variety of materials may be used, including DMSO cocktails, propylene glycol and the like.

Addressing the structure shown in FIGS. 5A and 5B, handpiece 110 includes an outer housing 112 and an inner chamber defined by an inner housing 114, the inner housing optionally comprising (for example) a stainless steel tube having an outer diameter of 0.14 inches and an inner diameter of 0.12 inches. The outer housing 112 in part defines an applicator for applying both heat and a cryoprotectant material to dermal tissues, the inner and outer housing together defining a space therebetween for a passage of an infusion fluid from an input port 116 (such as a Luer fitting) to a plurality of infusion and needles 118. In the exemplary embodiment, the outer housing 112 comprises a stainless steel tubing having an outer diameter of 0.20 inches and an inner diameter of 0.18 inches. A heater 120 is thermally coupled to the infusion fluid between the inner and outer housings, warming the fluid infused by infusions needles 118 and providing skin engaging surface 52 with a temperature of about 45° C.

The tissue-penetrating needle cooling probes 54 may comprise 30 g needles with blocked distal ends and having a length of about 3 mm. Fluid infusion needles 118 may comprise 30 g needles having a length of about 1.5 mm. In general, the spacing between tissue-penetrating cooling treatment probes 54 may be between about ¼ mm and 2 mm, preferably having a needle-to-needle spacing of between about ½ mm and 1 mm, ideally being about ½ mm. Where fluid infusion needles 118 are provided, they may be interspersed between at least some of the adjacent cooling treatment probes 54 and/or around a perimeter of the cooling treatment probes to limit the lateral spread of cooling.

As illustrated in FIG. 5B, the distal portion of a multi-needle probe handpiece with saline or other fluid infusion may again have needle probes 54 extending through the dermis 98 and epidermis 96 to a treatment zone, here in the hypodermis 130. Treatment zones may generally be defined by the temperature profiles 132 in the cooled tissues adjacent the distal portion of the cryogenic cooling needle probes 54. Warm saline 134 infused into the dermis 98 and/or epidermis 96 by infusion needles 118 may limit collateral injury to these tissues between treatment zones 132 and the skin surface 136.

As can be understood with reference to the temperature profiles illustrated in FIG. 5B, treatment zones 132 may provide desired temperatures in selected volumes or patterns of the target tissue, with adjacent target tissue regions being below or above the target treatment temperatures. As can be understood with reference to FIGS. 6A and 6B, applying cooling from a tissue-penetrating cryogenic probe in which cooling is applied primarily or entirely through a distal portion of the probe can also help limit cooling injury to the tissues adjacent the skin surface. Advantageously, the temperature profiles can, to a significant extent, be determined by selecting a probe surface temperature, a cooling treatment time, a needle-needle spacing, a probe and insulation geometry, and the like.

Figure 6A:
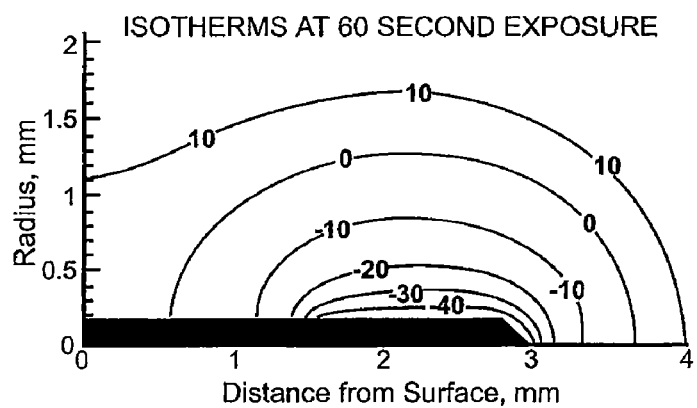
FIGS. 6A and 6B graphically illustrate temperature distributions measured from a center line of a tissue-penetrating cryogenic cooling probe.
Figure 6B:
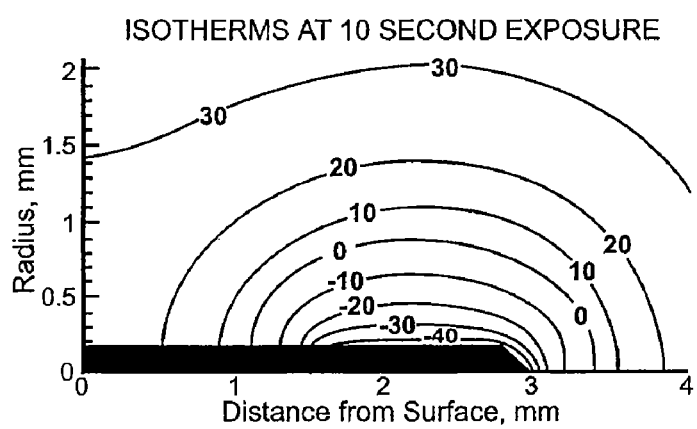

FIG. 6A shows isotherms of tissues, as measured from a center of a tissue-penetrating probe, after 60 seconds of exposure to cooling at −50° C. of probe surface temperature. The tissues along the skin surface reach a minimum temperature of below 10° C. and above 0° C. A similar plot of tissue temperature isotherms after 10 seconds of cooling exposure provides surface tissue temperatures above 20° C., as illustrated in FIG. 6B. Application of energy or suitable materials to collateral tissues may further tailor the shape of the tissue remodeling effect. Alternatively, damage to the tissues along the skin surface and the like may be limited by effecting the desired cosmetic result utilizing temperature ranges and/or times which inhibit damage to the collateral tissues.

As indicated above, a variety of methods may be used to protect the skin at the epidermal and/or the endodermal layers. For example, a delivery probe with multiple temperature zones may be used, the zones optionally corresponding to probe materials and/or insulation. In some embodiments, insulation (optionally segmented) may be built into delivery device; injection of saline or other heated biocompatible fluid may be provided; injection of biocompatible cryoprotectant may be provided; and/or the application of energy may be provided to limit collateral tissue damage.

Still further alternative mechanisms may be used to limit collateral tissue damage, optionally by enhancing the effects of cooling or other remodeling upon the target tissues. In some embodiments, it may be advantageous to enhance subthermal ice formation and/or heat conduction. Fat has insulation properties, and saline can be 3× as conductive as fat, so that adding saline (or other conductive agents) may help with freezing of some target tissues, including adipose tissues. Hence, injection of saline or some other material may enhance thermal conductivity and cooling remodeling efficacy and/or target region control. The injection of such materials to spread remodeling efficacy across a broader anatomical region may be particularly desirable. In some embodiments, saline may be infused by or adjacent to the cooling needles or tissue-penetrating probes 54. The cooling front may preferentially travel through the saline. Below 0° C. or solidification of the saline, the saline may still be approximately three times as conductive of heat as fatty tissues. Injection or other application of compounds may also enhance desired remodeling of the tissue via other mechanisms. For example, application of hypertonic solutions such as saline having sufficient salinity may enhance the effects of cold or heat on target tissues by altering a size of cells, dehydrating cells, and or the like. In some embodiments, application of such hypertonic solutions may effect the desired remodeling of target tissues without application of cold or heat.

Embodiments can apply cooling with at least one small, tissue-penetrating probe, the probe often comprising a needle (e.g., needle probe) having a size suitable for inserting through an exposed surface of the skin of the patient without leaving a visible scar following treatment. Treatment may be applied along most or all of the insertable length of the elongate needle, optionally by introducing cryogenic cooling fluid into the needle lumen through a small, tightly-toleranced lumen of a fused silica fluid supply tube, with the tube lumen often meeting the cooling fluid. Treatment temperature and/or time control may be enhanced using one or more valves, such as a simple pressure relieve valve coupled to the needle lumen via a limited total exhaust volume space.

Figure 10:
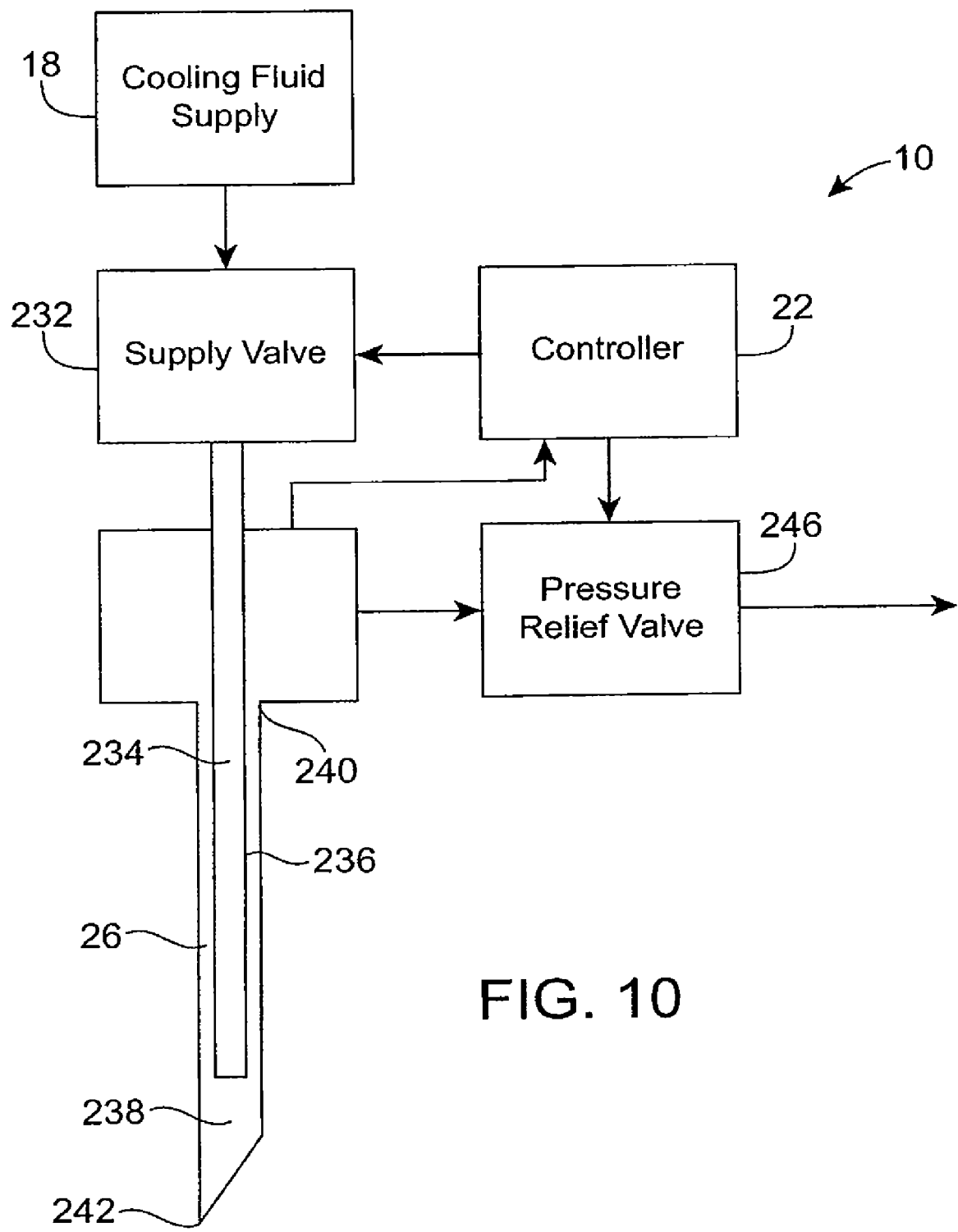
FIG. 10 schematically illustrates components that may be included in the treatment system.

Referring now to FIG. 10, the flow of cryogenic cooling fluid from fluid supply 18 is controlled by a supply valve 232. Supply valve may comprise an electrically actuated solenoid valve or the like operating in response to control signals from controller 22, and/or may comprise a manual valve. Exemplary supply valves may comprise structures suitable for on/off valve operation, and may provide venting of the cooling fluid path downstream of the valve when cooling flow is halted so as to limit residual cryogenic fluid vaporization and cooling. More complex flow modulating valve structures might also be used in other embodiments.

The cooling fluid from valve 232 flows through a lumen 234 of a cooling fluid supply tube 236. Supply tube 236 is, at least in part, disposed within a lumen 238 of needle 26, with the supply tube extending distally from a proximal end 240 of the needle toward a distal end 242. The exemplary supply tube 236 comprises a fused silica tubular structure 236a having a polymer coating 236b (see FIG. 11A) and extends in cantilever into the needle lumen 238. Supply tube 236 may have an inner lumen with an effective inner diameter 236c of less than about 200 μm, the inner diameter often being less than about 100 μm, and typically being less than about 40 μm. Exemplary embodiments of supply tube 236 have inner lumens of between about 15 and 50 μm, such as about 30 μm. An outer diameter or size 236d of supply tube 236 will typically be less than about 1000 μm, often being less than about 800 μm, with exemplary embodiments being between about 60 and 150 μm, such as about 90 μm or 105 μm. The tolerance of the inner lumen diameter of supply tubing 236 will preferably be relatively tight, typically being about +/−10 μm or tighter, often being +/−5 μm or tighter, and ideally being +/−3 μm or tighter, as the small diameter supply tube may provide the majority of (or even substantially all of) the metering of the cooling fluid flow into needle 26.

Though supply tubes 236 having outer jackets of polyimide (or other suitable polymer materials) may bend within the surrounding needle lumen 238, the supply tube should have sufficient strength to avoid collapsing or excessive blow back during injection of cooling fluid into the needle. Polyimide coatings may also provide durability during assembly and use, and the fused silica/polymer structures can handle pressures of up to 100 kpsi. The relatively thin tubing wall and small outer size of the preferred supply tubes allows adequate space for vaporization of the nitrous oxide or other cooling fluid within the annular space between the supply tube 36 and surrounding needle lumen 238. Inadequate space for vaporization might otherwise cause a buildup of liquid in that annular space and inconsistent temperatures. Exemplary structures for use as supply tube 36 may include the flexible fused silica capillary tubing sold commercially by Polymicro Technologies, LLC of Phoenix, Ariz. under model names TSP, TSG, and TSU, optionally including model numbers TSP 020090, TSP 040105, and/or others.

Figures 11, 11A:
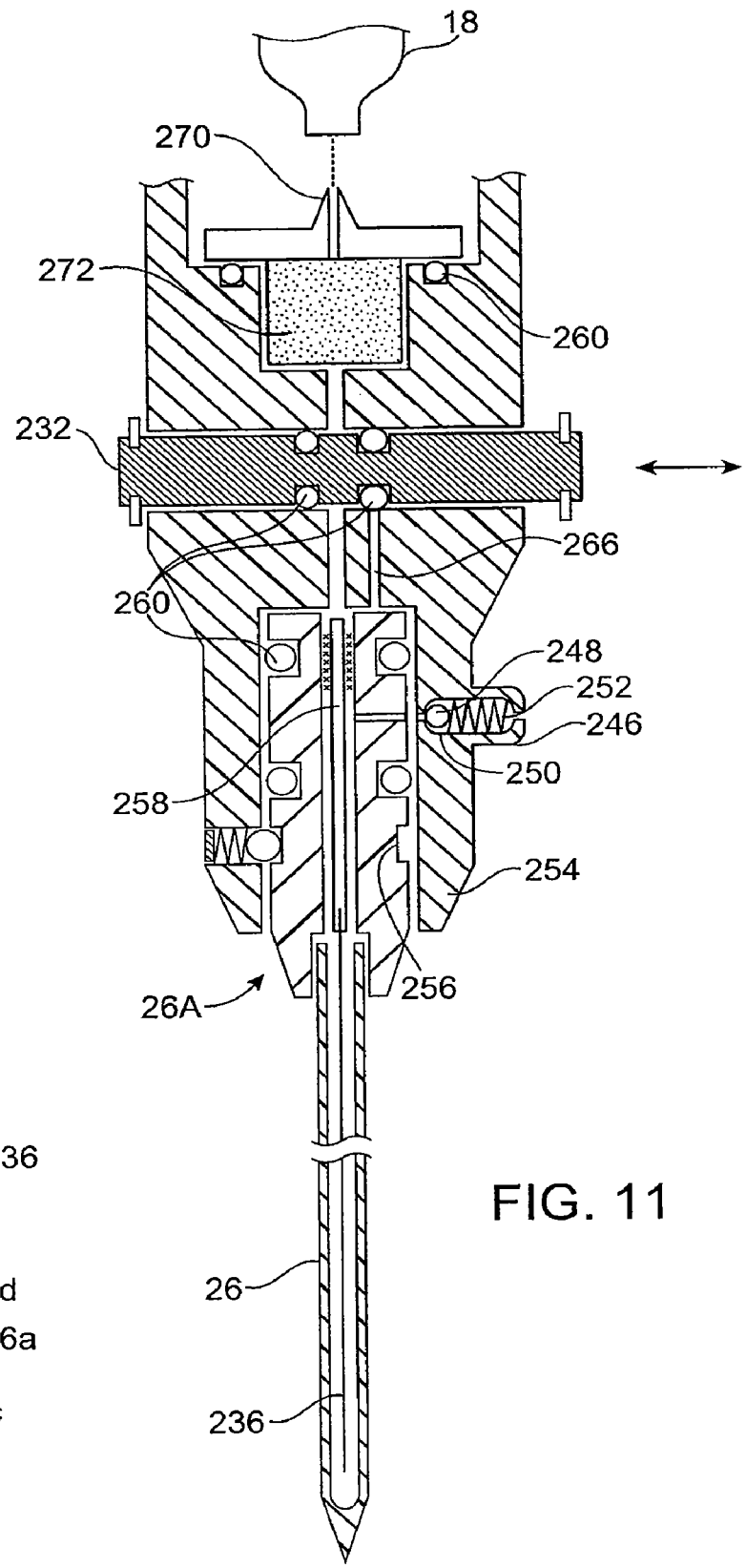
FIG. 11 is a schematic cross-sectional view of an embodiment of a distal portion of the probe and system of FIG. 1C, showing a replaceable needle and a pressure relief valve with a limited exhaust volume.
FIG. 11A illustrates an exemplary fused silica cooling fluid supply tube for use in the replaceable needle of FIG. 11.

Referring now to FIGS. 10 and 11, the cooling fluid injected into lumen 238 of needle 26 will typically comprises liquid, though some gas may also be injected. At least some of the liquid vaporizes within needle 26, and the enthalpy of vaporization cools the tissue engaged by the needle. Controlling a pressure of the gas/liquid mixture within needle 26 substantially controls the temperature within lumen 238, and hence the treatment temperature range of the tissue. A relatively simple mechanical pressure relief valve 246 may be used to control the pressure within the lumen of the needle, with the exemplary valve comprising a valve body 248 (here in the form of a ball bearing) urged against a valve seat 250 by a biasing spring 252.

During initiation of a cooling cycle, a large volume along the cooling fluid pathway between the exit from the supply tube and exit from the pressure relief valve 246 may cause excessive transients. In particular, a large volume in this area may result in initial temperatures that are significantly colder than a target and/or steady state temperature. This can be problematic, particularly when (for example) the target temperature is only slightly warmer than an undesirable effect inducing temperature, such as when remodeling through apoptosis or the like while seeking to inhibit necrosis. To limit such transients, the pressure relief valve 246 may be integrated into a housing 254 supporting needle 26, with the valve spring 252 being located outside the valve seat (and hence the pressure-control exit from pressure relief valve 246). Additionally, where needle 26 is included in a replaceable needle assembly 26A, pressure relief valve 246 is also located adjacent the interface between the needle assembly and probe handpiece housing 254. A detent 256 may be engaged by a spring supported catch to hold the needle assembly releasably in position, and the components of the needle assembly 26A (such as a brass or other metallic housing, a polyimide tubing 258, needle 26, and the like) may be affixed together using adhesive. Alternatively, as illustrated in FIG. 1C, the needle assembly and handpiece housing may have corresponding threads for mounting and replacement of the needle assembly. O-rings 260 can seal the cooling fluid pathway.

Very fine needles will typically be used to deliver to cooling at and/or below the surface of the skin. These needles can be damaged relatively easily if they strike a bone, or may otherwise be damaged or deformed before or during use. Fine needles well help inhibit damage to the skin during insertion, but may not be suitable for repeated insertion for treatment of numerous treatment sites or lesions of a particular patient, or for sequential treatment of a large area of the patient.

It may be advantageous to increase the volume of tissue treated by a single treatment cycle. As it is often desirable to avoid increasing the needle size excessively, along with selecting needles of different lengths, needle assemblies having differing numbers of needles in a needle array may also be selected and mounted to the probe body. Other embodiments may employ a single needle array fixedly mounted to the probe body, or a plurality of replaceable needle assemblies which all include the same number of needles. Regardless, cooling fluid flow to a plurality of needles may be provided, for example, by inserting and bonding a plurality of fused silica supply tubes into a 0.010 polyimide tubing 258 or header within the needle assembly, and by advancing the distal end of each supply tube into a lumen of an associated needle 26. The needles might vent into a common exhaust space coaxially around polyimide tubing 258 in a manner similar to the single needle design shown. This can increase the quantity of tissue treated adjacent and/or between needles.

Figure 12:
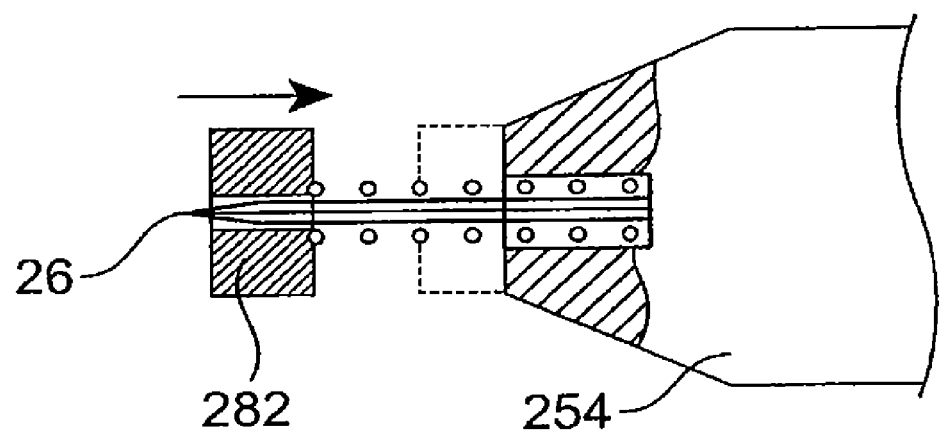
FIGS. 12 and 13 illustrate skin-engaging surfaces that selectably limit an effective insertable length of the needle, that apply pain-dulling pressure, and that apply inflammation-inhibiting cooling to the skin before and/or during treatment of the target tissue, respectively.

Referring now to FIG. 12, the application of pressure before, during, and/or after cooling may help dull or otherwise inhibit sharp pain. Such pain may otherwise result from the skin penetration, cooling, or thawing of the target and/or collateral tissues. It may also be beneficial to obscure the patient's view of the cooling needles, and/or to cover the needles when not in use so as to inhibit needle-stick injuries and potential disease transmission. Toward that end, skin-engaging surface 282 may be supported by an articulatable support structure having a first configuration (shown in solid in FIG. 12) and a second configuration (shown dashed in FIG. 12). A simple spring mechanism may be used to apply a desired contact force between the skin-engaging surface 282 and the patient before insertion and during cooling. More sophisticated arrangements can also be employed in which the needle is driven distally and then proximally relative to the skin engaging surface appropriate times after sufficient pressure is applied to the patient, and the like.

Figure 13:
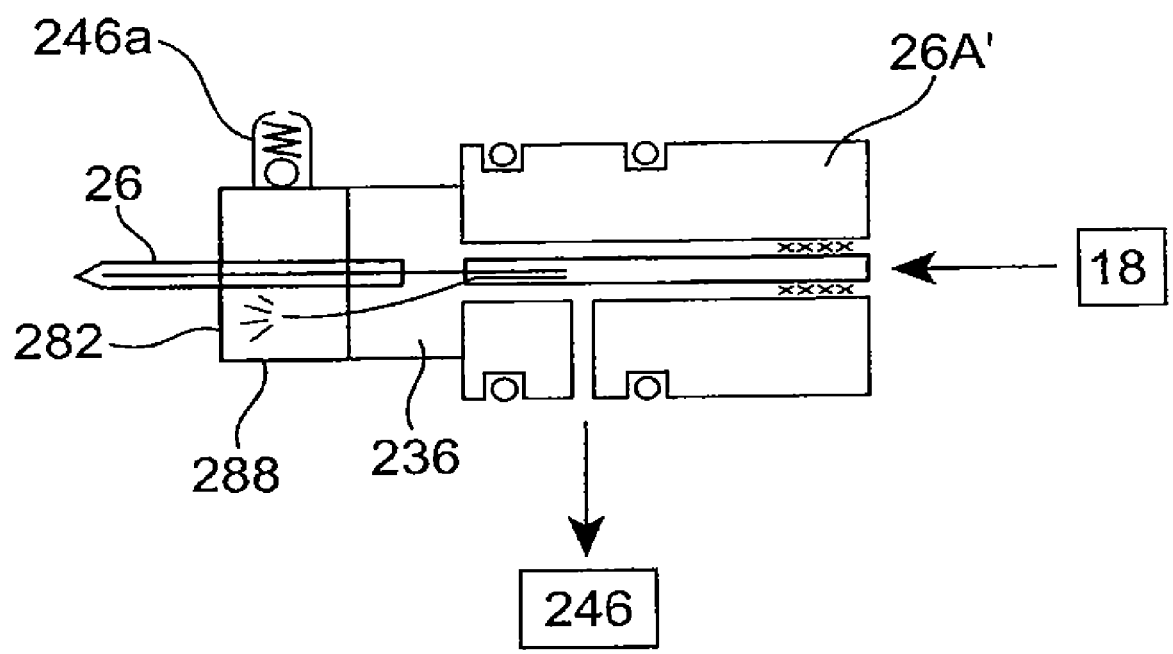

Referring now to FIG. 13, still further alternative embodiments may be provided, in this case to apply different cooling temperatures to the patient, and/or to apply cooling to the skin surface and to a target tissue adjacent needle 26. For example, in the case of acne it may be desirable to have two different cooling target temperatures, with cooling on the skin surface to inhibit inflammation (such as to about −10° C.), and (see FIG. 14) cooling of a target tissue TT cylinder around needle 26 sufficient to kill bacteria in the sebaceous gland and enlarged follicle opening (such as to about −20° C.). This dual temperature treatment may be particularly beneficial for severe forms of acne involving cysts or nodules. To provide cooling of tissue engaging surface 282, that surface may be thermally coupled to a chamber 288. Cooling fluid may be transmitted into chamber 288 by a port of a cooling fluid supply tube 236, and the pressure of chamber 288 (and hence the temperature within the chamber) can optionally be controlled by a dedicated additional pressure relief valve 246a. As the pressure within chamber 288 may differ from that within the needle, different treatment temperatures may be provided. The structures described herein can also be combined, for example, with the dual skin surface/needle temperature treatment structure of FIG. 13 being compatible with the replaceable needle systems of FIGS. 1C and/or 11. The dual skin surface/needle treatment systems and methods may also be compatible, for example, with the articulatable skin surface supports of FIG. 12 so as to apply cooled pressure to the skin prior to and/or during needle insertion using a flexible fluid supply tube or the like.

Figure 18:
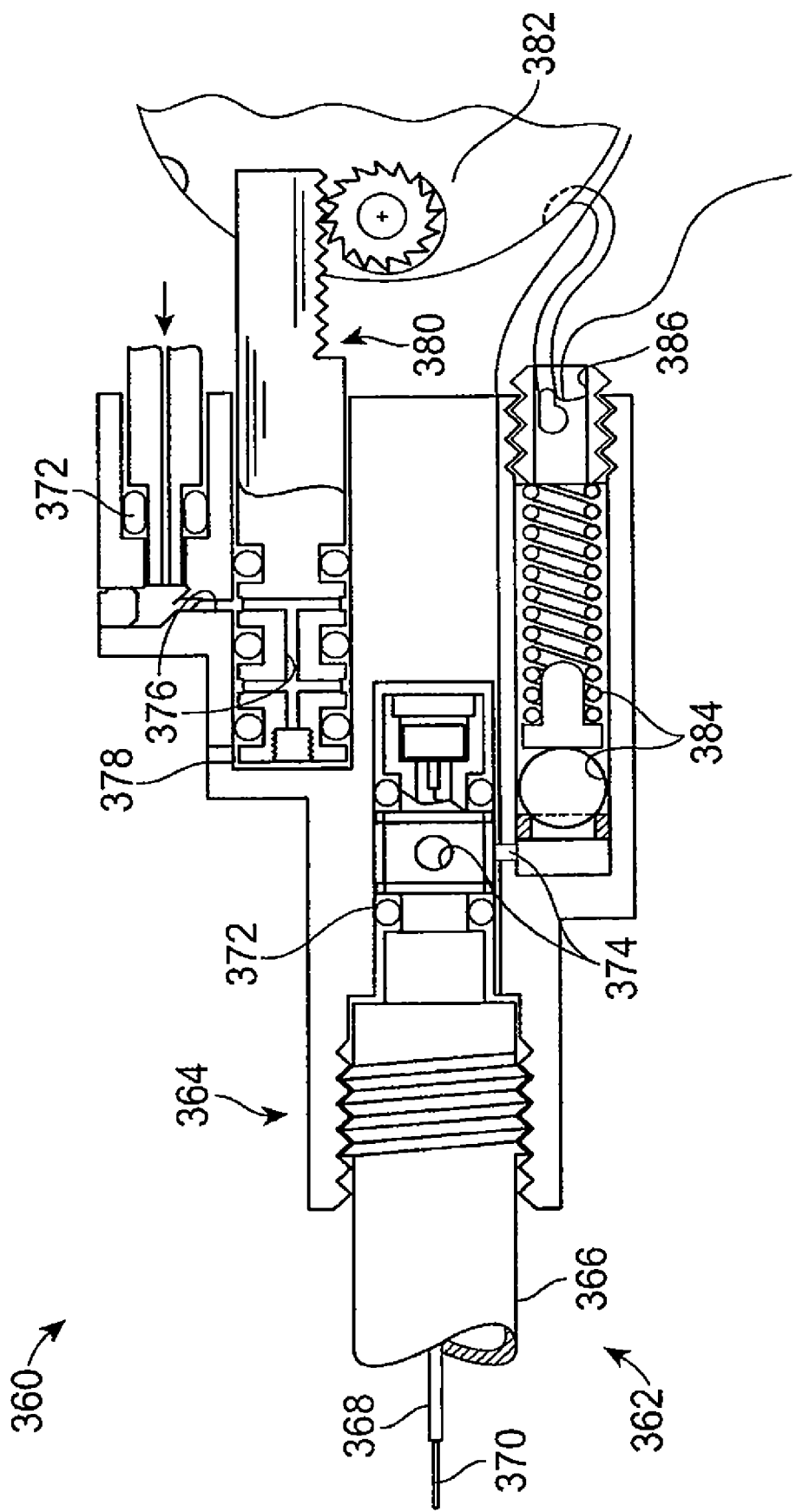
FIG. 18 is a schematic cross-sectional view showing an alternative exemplary needle interface, along with the adjacent structures of the needle assembly and probe body.

Referring now to FIG. 18, an exemplary interface 360 between a cryogenic cooling needle probe 362 and the associated probe body structure 364 are illustrated, along with adjacent portions of the needle, valve, probe body, and the like. Needle probe 362 is included in a needle assembly having a needle 366 with a lumen containing a polyimide coating or jacket 368 around a fused silica cooling fluid supply tube 370. O-rings 372 seal in exhaust gas path 374 and inlet cooling fluid path 376, with the inlet path having a vent 378 to minimize run-on cooling when the cooling fluid supply is shut off by a valve 380, as generally described above. The valve is here actuated by a motor 382, while the exhaust gas pressure is controlled using a biasing spring and ball valve 384 as described above. A hollow set screw 386 can be used to assemble and/or adjust the pressure relief valve, and a thermistor 388 can be used to sense cooling gas flow. Cooling gas flow and, therefore, treatment temperature can be selected and/or modified, for example, by modifying the position of the set screw 386.

Still further alternatives may also be provided, including systems that generate a high rate of cooling to promote necrosis of malignant lesions or the like. High cooling rates limit osmotic effects in the target tissue. Slow cooling may tend to promote ice formation between cells rather than within cells due to the osmotic effect. While such slow cooling can be provided where necrosis is not desired (such as through the use of a proportion supply valve to modulate flow, a processor generated on/off cycle during initial cooling, or the like), the needle probes described herein will often be well suited to induce rapid cooling rates of the target tissue by vaporizing the cooling fluid in close thermal and spatial proximity to that target tissue. Hence, where necrosis of cells by intracellular ice formation is desired, cooling rates of about 25° C./sec or more, or even about 50° C./sec or more can be provided.

Permanent and/or temporary muscular function inhibition may be employed. A temporary effect can be used on a trial basis to avoid long term injuries or undesirable outcomes. A permanent effect may be desirable to minimize cost and avoid repeated treatments. Desired temperature ranges to temporarily and/or permanently disable muscle, as well as protect the skin and surrounding tissues, may be indicated by Table 2 as follows:

TABLE 2

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | tissue damage | Phase transition begins |
| −2° C. | | minimal apoptosis |
| −3° C. | | Peak phase transition |
| −5° C. | | moderate apoptosis |
| −8° C. | | Completion of phase transition |
| −10° C. | | mild apoptosis; considerable apoptosis |
| −15° C. | | moderate apoptosis; extensive apoptosis mild-moderate necrosis |
| −40° C. | | extensive necrosis |

To overcome the potential for an undesirable outcome, treatments may be administered in a controlled manner, a little at a time over the course of several procedures. Where muscle is concerned, a temporary loss of elasticity through changes in the morphology of the collagen and elastin may be seen with the onset of ice formation. The degree to which there is a loss of movement is likely to increase as a greater percentage of cells are affected. This can be controlled by varying treatment parameters such as times, rates, and temperatures. The lower the temperature, the higher the percentage of cells is that undergo the contraction-inhibiting effect.

In light of the above, and so as to provide cosmetic tissue remodeling with a desired or selected efficacy duration, tissue treatment temperatures may be employed per Table 3 as follows:

As can be understood with reference to FIGS. 5B, 6A, and 6B, some tissues may be exposed to temperatures above or below the desired treatment range, and varying effects on tissues may occur, particularly including some necrosis when using colder temperatures.

There is also a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of these apoptosis and necrosis may also provide long-lasting or permanent.

Apoptosis, alternately termed "programmed cell death", is a gene-directed self-destruct mechanism by which cells die without adversely affecting surrounding tissues. It is characterized by a well-ordered sequence of events, including chromatin condensation, nuclear fragmentation, and membrane blebbing. Apoptosis plays a number of roles in the development and regulation of healthy tissue. As part of normal tissue development and differentiation, apoptosis is part of a strategy to select certain cells for survival, thereby sculpting a tissue's specificity. In mature tissue, apoptosis balances cell division to prevent excess tissue growth.

Another role of apoptosis is to ensure that injured or mutated cells do not proliferate. Environmental or physiological stimuli which damage the cell may induce or activate the genetic program for apoptosis. Specifically, injurious external stimuli (such as cold exposure) can activate the genes which drive the apoptotic cascade of events. Apoptosis can be elicited by a physiological stimulus that is not per se harmful

TABLE 3

| Cooled Temperature Range | Time Effectiveness | Purpose |
|---|---|---|
| ≧0° C. | Treatment lasts only while the needle is inserted into the target tissue. | Can be used to identify target tissues. |
| From 0° C. to −5° C. | Often lasts days or weeks, and target tissue can repair itself. Embodiments may last hours or days. | Temporary treatment. Can be used to evaluate effectiveness of remodeling treatment on skin surface shape or the like. |
| From −5° C. to −15° C. | Often lasts months to years; and may be permanent. Limited muscle repair. Embodiments may last weeks to months. | Long term, potentially permanent cosmetic benefits. Can be deployed in limited doses over to time to achieve staged impact, controlling outcome and avoiding negative outcome. May be employed as the standard treatment. |
| From −15° C. to −25° C. | Often lasts weeks or months. Muscle may repair itself via satellite cell mobilization. Embodiments may last years. | May result in Mid-term cosmetic benefits, and can be used where permanent effects are not desired or to evaluate outcomes of potentially permanent dosing. Embodiments may provide permanent treatment. | and that causes death to only a specific population of cells and that causes death to only a specific population of cells and various forms of cellular injury, whether induced by immune effector cells, aberrant metabolic processes, chemotherapeutic drugs or temperature shifts, can result in common morphological changes including the formation and shedding of membrane vesicles from the injured cell surfaces, and/or apoptosis.

In other words, normal cells may be genetically programmed with a suicide routine, leading to the term "programmed cell death". This programming can be activated or triggered by non-lethal cold exposure. Alternative mechanisms may also be used to trigger apoptosis, including appropriate chemical or heat exposure as well as hypoxia induced stress by loss of vascular perfusion. Therefore, cryo-treatment and other methods can accurately be described as inducing or triggering apoptosis.

For the reduction of adipose tissue, a permanent effect may be advantageous. Surprisingly, both apoptosis and necrosis may produce long-term or even permanent results in adipose tissues, since fat cells regenerate differently than muscle cells. This also applies to reduction in mass for scars, lesions, and skin tissue.

Aspects of healing which can be helpful for these treatments include the four phases of healing: inflammation (immediate); substrate (6 hours); repair (5-6 days); and maturation. Return of at least some muscular strength in normal healing typically occurs in 4-6 days after injury, and may peak 14-16 days. Scarring in tendons can cause lengthening, thereby inhibiting contractions of an associated muscle. More, specifically separation injury may result in growth of new tissue to reconnect, resulting in increased length and loss of contractility (and hence a flaccid muscle). Healing can occur through both fibrosis and regeneration of myofibrils. Scar tissue can strangle myofibrils, preventing regeneration. Between muscle ends, scar tissue can elongate resulting in poor contractility. Similarly, any break in a chain of connective tissue can inhibit contractions, including in a ligament or tendon. Ligaments can have an ability to reform, closely approximating the original pre-treatment structure. Like tendon, if ends (of severed injury) don't heal together, elongation can occur leaving it weak. Non-severed injury may effectually be similar to a sutured break which does not elongate.

It will be recognized that the methods of the present invention can be directed to a variety of target tissues and are not limited to any particular tissue. Target tissues amenable to treatment according to the present invention can include, for example, tissues that have been subjected to cryogenic or cryosurgical treatments using previously known techniques for delivering cooling energy to tissues (e.g., open spray, touch probe). See, e.g., *Cutaneous Cryosurgery: Principles and Clinical Practice* (3rd Edition); Jackson et al., CRC Press, 2005. Target tissues can typically include dermatological tissues and/or subcutaneous tissues. For example, a target tissue can include a patient's skin, including an outer surface of the patient's skin as well as tissues of the skin located below the skin surface. In one embodiment, for example, a needle probe can be advanced distally so as to penetrate into the patients skin, e.g., through a surface of the skin and cooling energy directed to the skin surface and/or to tissue below the skin, including tissues at various depths of penetration into or through the skin surface and into or through the skin tissue itself.

As set forth above, target tissues can include skin, muscles or muscle containing tissues, nerves, connective tissue, as well as adipose tissues. Target tissues can also include various types of lesions, wounds, and the like. Target tissues can include cancerous lesions, malignant or premalignant lesions, or tissues having cells either exhibiting or predisposed to exhibiting unregulated growth. Target tissues can additionally include benign lesion. Non-limiting examples of benign lesions amenable to treatment according to the present invention can include the following: acne; adenoma sebaceum; alopecia areata; angiokeratoma; angiolymphoid hyperplasia; cherry angioma; chondrodermatitis nodularis helices; clear cell acanthoma; cutaneous horn; dermatofibroma; dermatosis papulosa nigrans; disseminated superficial actinic keratosis; elastosis perforans serpiginosa; epidermal naevus; granuloma annulare; granuloma faciale; haemangioma; herpes labialis, recurrent; hidradenitis suppurativa; hyperhidrosis, axillary; hypertrophic scar; idiopathic guttate melanosis; ingrowing toenail; keloid; kyrle's disease; leishmaniasis; lentigines; lentigo simplex; lichen planus, hypertrophic; lichen sclerosus, vulva; lichen simplex; lichenoid keratosis, benign; lupus erythematosus, discoid; lymphangioma; lymphocytoma cutis; melasma; milia; molluscum contagiosum; mucocoele, mouth; myxoid cyst, digital; orf; pigmented naevi; porokeratosis; prurigo nodularis; pruritus ani; psoriasis, lichenified; pyogenic granuloma; rhinophyma; rosacea; sarcoid, granuloma; sebaceous hyperplasia; seborrhoeic keratosis; skin tags; solar atropy, keratosis, or lentigo; spider naevus; steatocystoma multiplex; syringoma; tattoos; trichiasis; trichoepithelioma; venous lakes; warts; or xanthoma.

As set forth above, embodiments of the present invention may be employed for a variety of conditions, including cosmetic conditions, for example, by inhibiting or ameliorating undesirable and/or unsightly effects that may be visible on the patient's skin (e.g., lines, wrinkles, cellulite dimples, lesions, scars, wounds, etc.) or on other surrounding or adjacent tissues. In one embodiment, directing of cooling energy according to methods of the present invention includes inhibiting contraction of a muscle of the target tissue. Delivery of cooling energy can have a variety of contraction inhibiting effects on the targeted muscle tissue and will not be limited to any particular mode or mechanism of action.

Without being bound by any particular theory, methods of treating a target tissue of a patient as described herein, including remodeling of the target tissue to improve a cosmetic appearance of the patient and/or inhibit contraction of a muscle of the target tissue, may include a variety of mechanisms of action. Particular mechanism and/or cooling mediated effects will be at least partially dependent upon the selected cooling energy for delivery. As set forth above, tissue cooling can be selected so as to induce apoptotic or apoptosis-mediated effect (e.g., non-inflammatory response). In some instances, however, delivery of cooling energy into a target tissue and remodeling of the target tissue can additionally or alternatively include induction of certain tissue conditions commonly observed in tissue freezing (e.g., frostbite) pathophysiology. For example, exposure of the target tissue to cooling energy can lead to ice crystal formation, cellular dehydration, protein denaturation, disruption of nucleic acid synthesis and/or repair, disruption of cell permeability, osmotic changes, and the like. Effects of cooling energy delivery may or may not continue following discontinuation of energy delivery. For example, removal of the needle probe can be followed by swelling, cell aggregation, endothelial cell damage, thrombosis, tissue edema, increased pressure, cell blebbing (e.g., as in apoptosis), localized ischemia and tissue death.

Figure 15A:
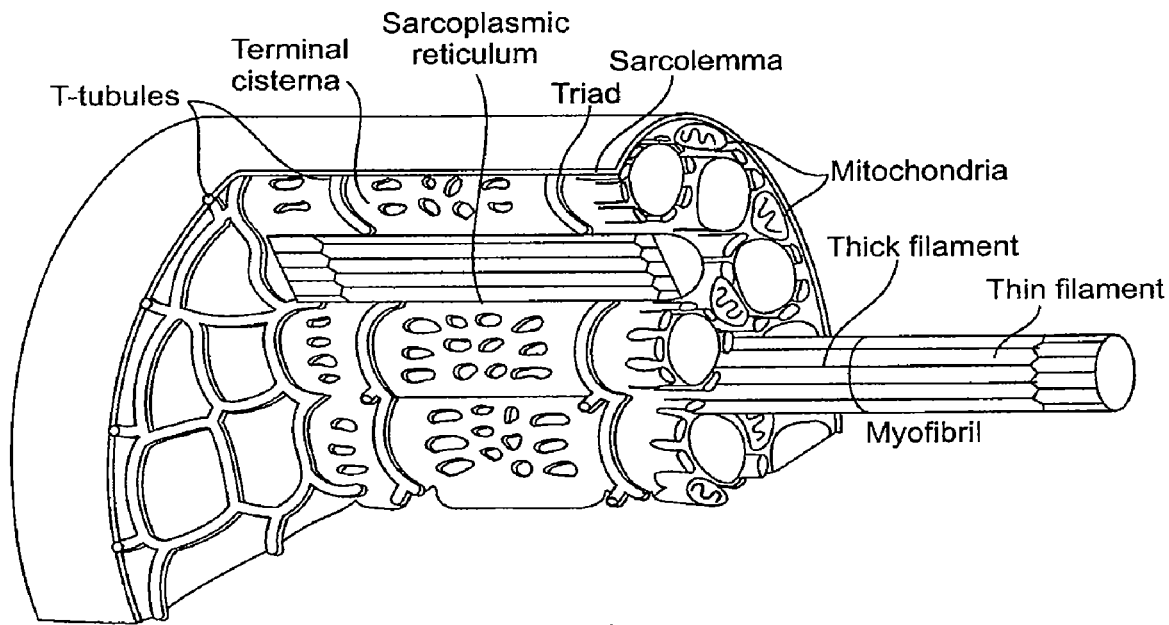
FIGS. 15A and 15B illustrate components of a muscle tissue.
Figure 15B:
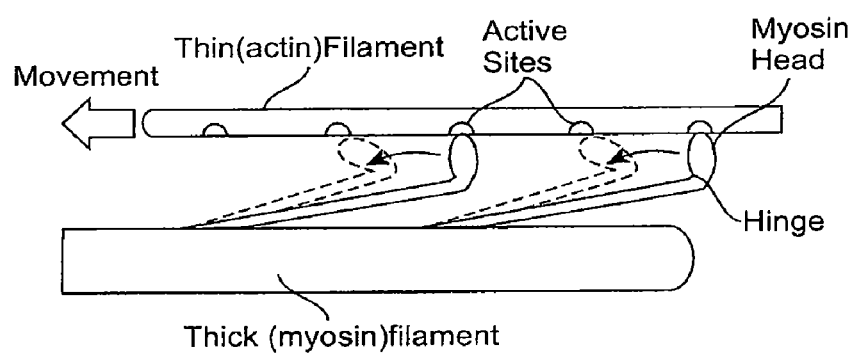

In one embodiment, tissue remodeling, including disrupting muscle contractile function or contractility, includes inducing protein denaturation in the target tissue. It will be recognized that contractility of a muscle typically involves muscle action occurring as a result of an interaction or "sliding" of filaments of the muscle. Muscle fibers are made up of protein filaments, including actin, myosin, troponin and tropomysin. Muscle contraction involves various protein structures of the muscle interacting with each other, including protein structures of the muscle sliding across each other to initiate compacting and shortening of the muscle unit and, therefore, muscle contraction. The interaction of muscle protein structures during muscle contraction can include myosin heads binding to actin thin filaments in the presence of calcium ions. The muscle contraction can include a sort of "ratchet action", in which myosin heads can move or flip inward causing a muscle fiber to shorten. See, e.g., FIGS. 15A and 15B.

Thus, in one embodiment, protein denaturation induced according to the present invention can disrupt the "ratchet action" of a muscle tissue, and can cause muscle proteins of the target tissue region to "unravel" or become structurally altered so as to modulate muscle function, but may remain substantially intact. Once the muscle protein(s) unravel or denature, the targeted muscle tissue does not have the structure necessary to interact mechanically with other filaments of the muscle unit, thereby rendering the target muscle non-functional or at decreased functional capacity compared to pre-treatment conditions. In some embodiments, protein denaturation may be induced using treatment temperatures from about 0° C. to about −25° C.

In yet another embodiment of the present invention, disruption and/or inhibition of muscle contractile function can include disruption of cellular signaling, such as calcium signaling, in the target tissue region. Calcium is a known chemical component involved in triggering protein action that causes muscle contraction (see above). Delivery of cooling energy and cooling of a target tissue according to the methods of the present invention can be selected so as to modulate calcium signaling and thereby disrupt or inhibit muscle contractile function. In one embodiment, cooling of the target tissue can be selected so as to induce a hypertonic environment in the target tissue during ice formation. Ice formation in a target tissue can be accomplished as described herein. For example, ice formation via the tissue cooling described herein can include freezing of extracellular saline. As the extracellular saline freezes it can reject solute (e.g., salt), thereby creating a hypertonic environment. Such a hypertonic environment can depress muscle function. In one embodiment, ice formation and depression of muscle function can be induced using treatment temperatures from about 0° C. to about −20° C. For example, saline freezes at about −1° C. and once frozen comprises a hypertonic environment. As temperatures below about −20° C. a hypertonic dehydrating effect on the cells may become less prevalent as intracellular ice formation and bursting of cells increases, and cells therefore become less responsive to hypertonicity.

Figure 16:
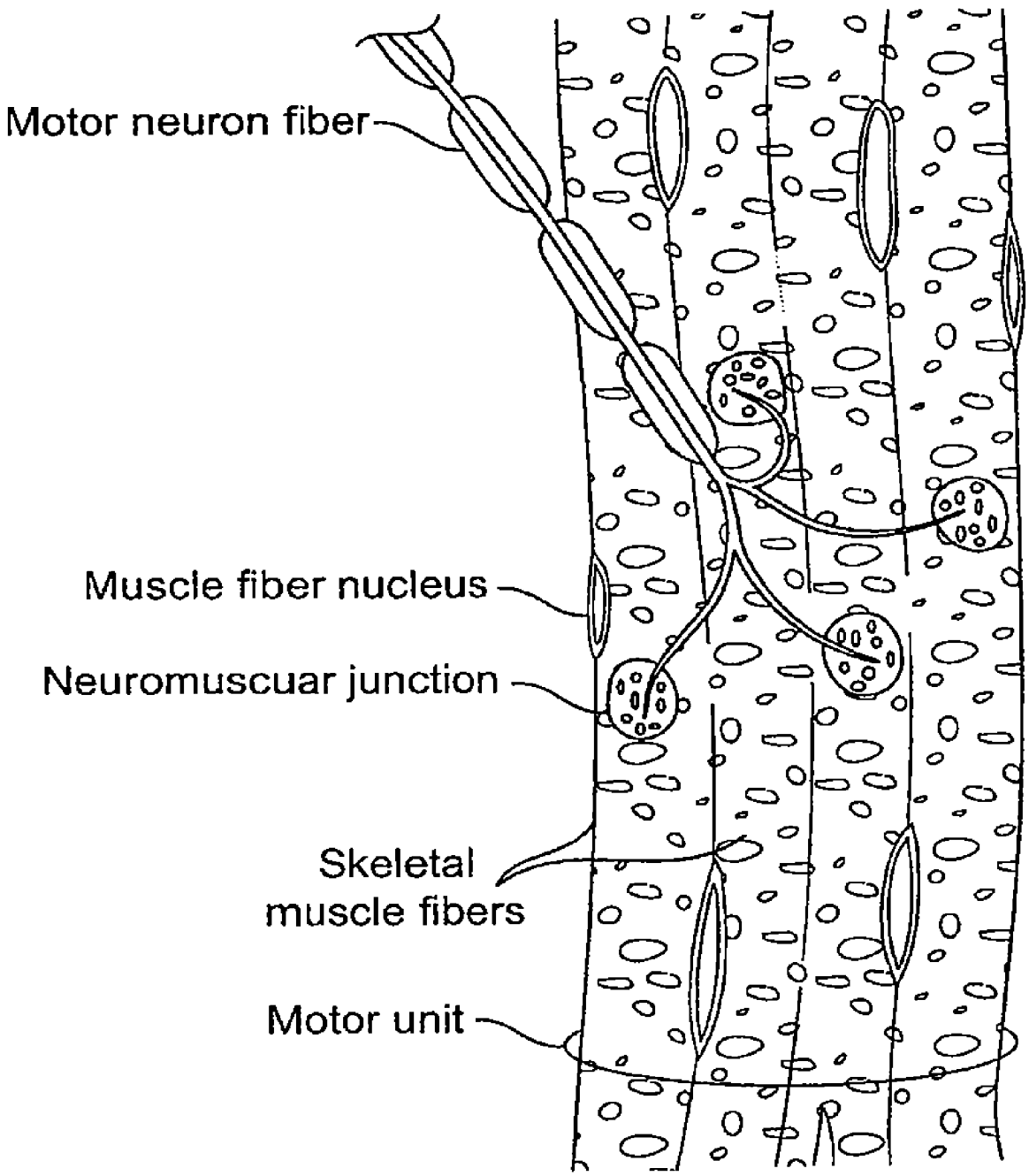
FIG. 16 illustrates tissue components of a muscle motor unit, including muscle fibers, a motor neuron fiber, a neuromusclular junction, and a muscle contractile chain.

According to another embodiment of the present invention, inhibition of muscle contraction can include disruption of electrical signaling and/or motor unit recruitment. A motor unit of a muscle, which includes multiple skeletal muscle fibers innervated by a motor neuron at a neuromuscular junction, is illustrated in FIGS. 2M and 16. A muscle will include a plurality of motor units. Fewer operating motor units or motor units operating in synchronicity can weaken a contractile force of a muscle. Such weakening of a muscle can cause tissue remodeling and/or alteration of the shape or cosmetic appearance of the patients skin (e.g., wrinkle formation). Thus, similar to wrinkle treatment with other methods (e.g., Botox™ based methods), a muscle does not necessarily have to be fully disabled to reduce a wrinkle, e.g., as indicated by electromyograms following Botox™ treatment showing that a reduction of muscle function but not an elimination of function or muscle contraction. Thus, both partial and more complete disabling of a muscle can reduce a skin wrinkle and alter the shape of a skin surface. A reduction in motor unit recruitment can be achieved, for example, by reducing muscle fiber activity and/or density (e.g., reducing the number of fibers in a motor unit), as well as by elimination of functioning neuromuscular junctions by eliminating them including, e.g., induction of apoptosis or necrosis in the target tissue.

Inhibition of muscle contraction can include disruption of electrical signaling and/or motor unit recruitment can include targeting treatment of a tissue region at the neuromuscular junction of a motor unit. As illustrated in FIG. 16, a neuromuscular junction is normally located near the center of the fiber. As a signal is released from the nerve to the muscle, it travels down the length of the fiber to induce muscle contraction. The signal can enter near the middle of the fiber at the neuromuscular junction and split off toward each end of the fiber(s). Selective placement or positioning of a needle or probe, or tissue cooling at or near the center of the muscle fiber or a neuromuscular junction can increase disruption of the ability of the muscle fiber to receive and relay the signal from the nerve. Further, disrupting and/or eliminating portions of the muscle fiber close to the neuromuscular junction can disrupt the signal from reaching at least a portion of the length of the fiber, thereby disrupting muscle fiber contractility. Thus, disruption of muscle fiber contractility can be accomplished with partial damage and in the absence of complete elimination of the muscle fiber.

In another embodiment, the cooling can be selected so as to induce a reduction in tissue mass, for example, during or proximate to the time of energy delivery or after removal of the probe from the patient. Reduction of tissue mass can include mass reduction of any type of tissue amenable to treatment according to the inventive methods described herein, including, for example, adipose tissue, nerve tissue, muscle tissue, skin tissue, tissue of a wound or lesion (e.g., benign lesion, benign lesion, scar tissue, acne, etc.), and the like. Without being bound by any particular theory, tissue reduction can occur with stimulation by the delivered cooling energy of apoptosis and/or necrosis in the target tissue, and resulting tissue healing responses, either during or near the time of energy delivery, or subsequent to energy deliver, such as after the needle probe has been removed from the patient. In one embodiment, for example, target tissue being treated can include adipose tissue and the cooling energy for deliver can be selected so as to reduce or eliminate adipose cells of the target tissue. Reduction of adipose tissue can include cooling the tissue so as to induce apoptosis and/or necrosis in the adipose cells of the target tissue, for example, to remove fat (e.g., microsculpt, macrosculpt) in areas of the patient's body where techniques such as liposuction might not be practical or feasible, including sensitive areas such as around or under the patient's eyes.

In another embodiment, target tissue mass reduction methods can include selectively reducing skin tissue in the patient's body. For example, using cold temperatures to create apoptosis in skin tissues trans-dermally could eliminate the treated tissue without inflammation or scarring. Such methods can be used to improve or enhance the cosmetic appearance of the patient. For example, on a small scale this could be performed to eliminate undesirable cosmetic skin features such as creases, wrinkles, and/or stretch marks, or to remove or "tighten" loose skin, such as jowls, loose neck skin (e.g., "chicken neck"), or droopy eyelids, and the like, as well as on a larger scale for loose skin, for example, under the arms, on the breast, on the abdomen, or loose skin following bariatric surgery. Such methods are unique for at least the reason of not necessarily seeking to stimulate collagen to eliminate the problem. On a larger scale, skin tissue reduction methods described herein can be used to reduce larger amounts of skin, such as undesirable excessive skin following surgical procedures such as bariatric or weight loss surgery.

Tissue reduction and treatment methods described herein can further be utilized for the reduction in mass and/or treatment of certain benign lesions, such as scars (e.g., keloid scars), acne, etc (see above). In one embodiment, scar tissue can include a surgically induced scar due to surgical treatment or procedure on the patient, and reduction in scar tissue can occur following surgery and during the healing process by exposing the tissue to cold temperature or cooling energy as described herein, and inducing, for example, apoptosis in the inflammatory tissues. In one embodiment, a needle probe of a device of the present invention can be inserted into a scar tissue, such as a keloid scar, at various angles and orientations for treatment. For example, the needle probe can be inserted into the scar tissue with the needle approximately parallel to the surface of the skin so as to laterally lance the scar and treat the inside of the scar tissue along the length of the scar while preserving the skin adjacent to and/or surrounding the scar, as well as tissues beneath the scar.

Figure 14:
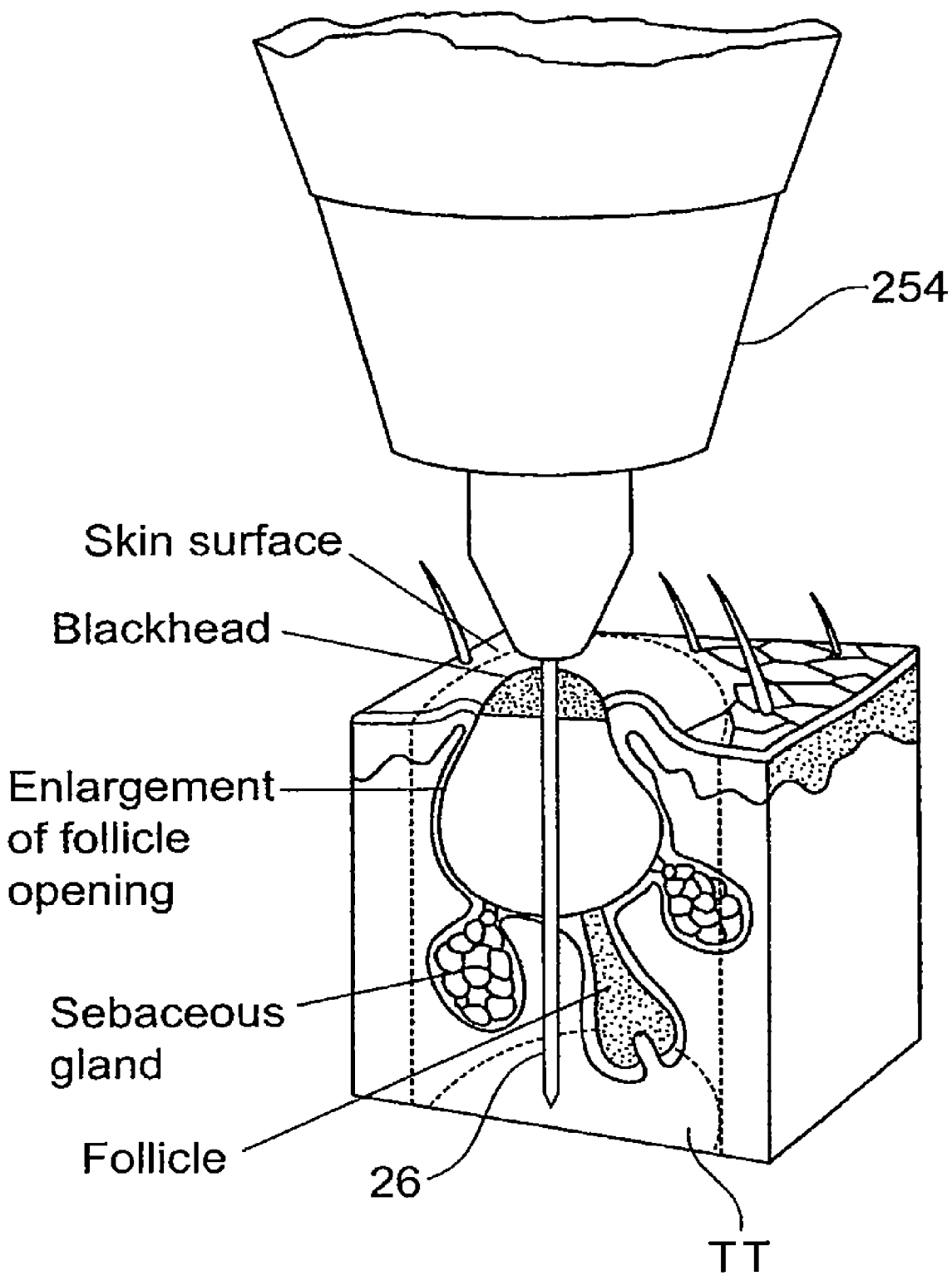
FIG. 14 schematically illustrates a cryogenic microprobe needle system being used for a dermatological treatment.

Methods of the present invention can also be utilized for the treatment of acne lesions, such as blackheads, whiteheads, papules, pustules, nodules, cysts, and the like (see, e.g., FIG. 14). Tissue cooling in the treatment of acne can be used, for example, in stimulating apoptosis, limiting inflammation, reducing or eliminating infection (e.g., bacterial infection), reducing or eliminating scarring or scar tissue, and the like. In some instances, it may be desirable to deliver multiple different cooling temperatures to the treated tissue (e.g., two or more different temperatures). For example, a first temperature on the surface of the skin (e.g., about −10 degrees C.) can be selected to help reduce inflammation in the target tissue and/or surrounding area, and a second temperature (e.g., about −20 degrees C., or below) can be selected and delivered below the surface of the skin so as to treat the infection and/or kill infecting bacteria. Such selection and delivery of multiple temperatures to the target tissue may be particularly effective with severe forms of acne like cysts or nodules.

Figure 17:
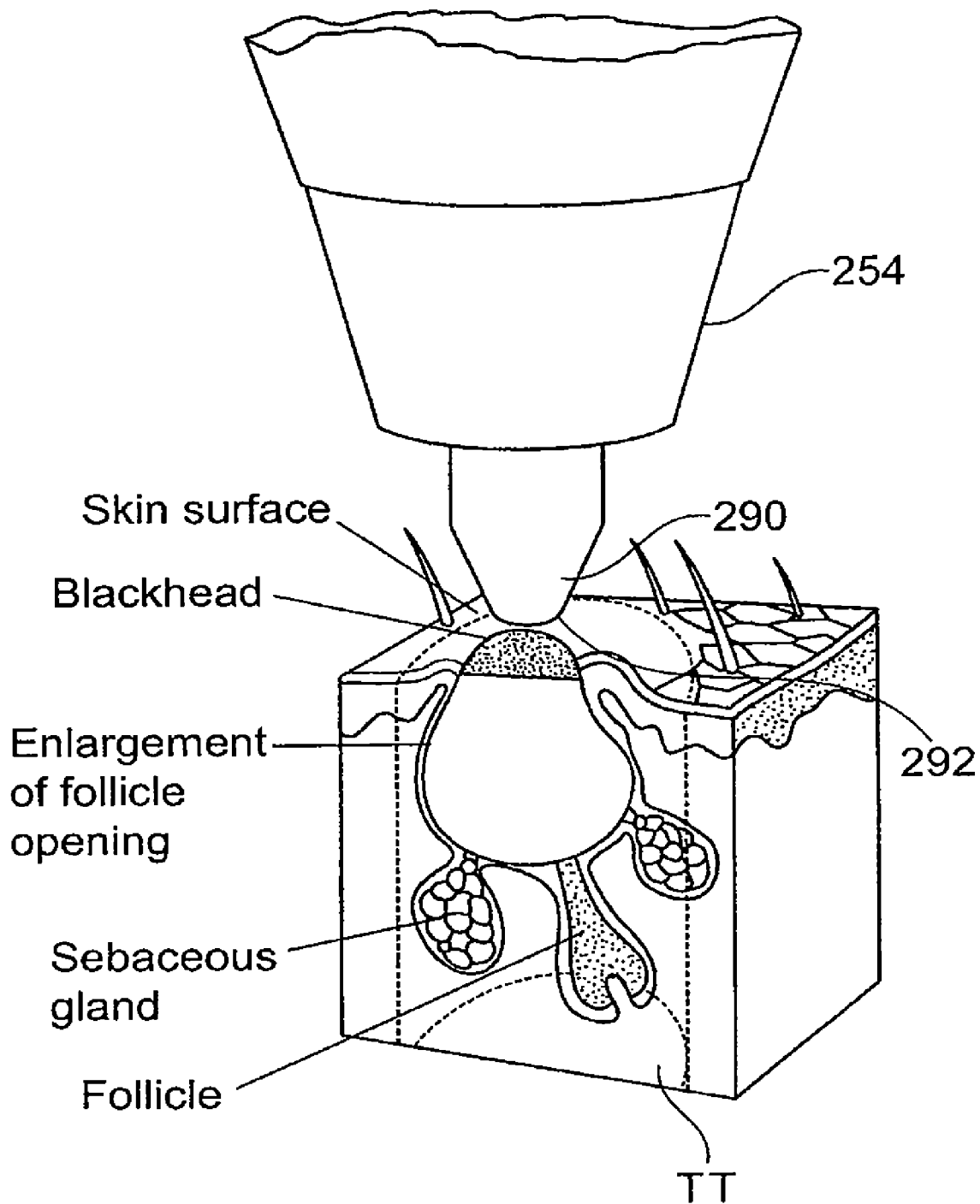
FIG. 17 schematically illustrates a non-penetrating cryogenic probe system being used for a dermatological treatment.

In some instances it may be desired to cool the target tissue, as described above, but without penetrating the target tissue with a cooling probe. As such, according to another embodiment, delivery of the cooling energy to the target tissue can be accomplished using a non-penetrating probe 290, as illustrated in FIG. 17. Rather than penetrating into the target tissue as with a needle electrode, the non-penetrating probe 290 is positioned in contact with a portion of the target tissue (e.g., skin surface), and cooling is directed through the probe and the cooling transferred to the target tissue. The probe 290 includes at least one tissue engaging surface 292 that is positioned in contact with the target tissue for tissue cooling. Systems and devices of the present invention having the non-penetrating probe configuration can be used, for example, for treating a target tissue comprising a lesion, such as an acne lesion. Similar to the above, tissue cooling in this manner can be used for treating and remodeling the acne lesion target tissue, for example, by stimulating apoptosis, reducing or eliminating infection or inflammation, reduction in scarring, and the like.

In yet another embodiment, delivery of the cooling energy can be selected to promote healing of the target tissue (e.g., lesion, wound, etc.). Without being bound by any particular theory, treatment of a wound (e.g., skin wound) with cooling energy or controlled cold temperatures/freezing can include cooling energy selected to induce apoptosis in the target tissue so as to aid in the healing process. Apoptosis is important to normal wound healing, including in the removal of inflammatory cells and scar tissue formation. As cell populations rapidly proliferate during tissue reconstruction, cell growth is balanced by apoptosis. Some cells, such as inflammatory cells, for example, must be removed in order to begin subsequent stages of wound healing. Persistent inflammation can lead to non-healing wounds, and granulation tissue typically must decrease in cellularity in order to develop into healed scar tissue. As such, delivery of cooling energy can be selected so as to induce apoptosis and/or remove inflammatory cells, and aid in the healing process, whereas the lack of apoptosis may slow or hinder the healing process around wounds, such as in non-healing ulcers and diabetic wounds.

Figure 7A:
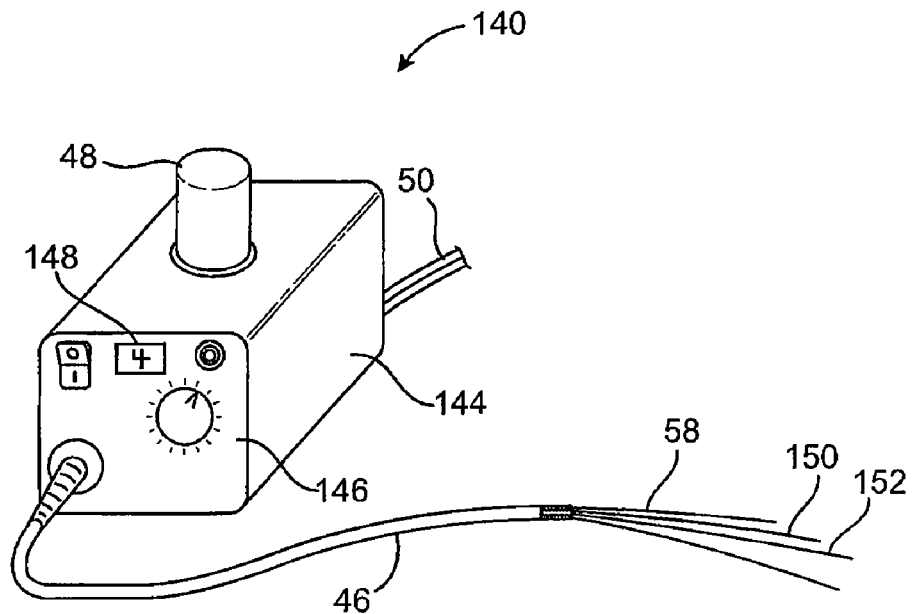
FIGS. 7A and 7B are perspective views schematically illustrating a proximal housing and a distal handle of another subdermal cryogenic remodeling system, respectively.
Figure 7B:
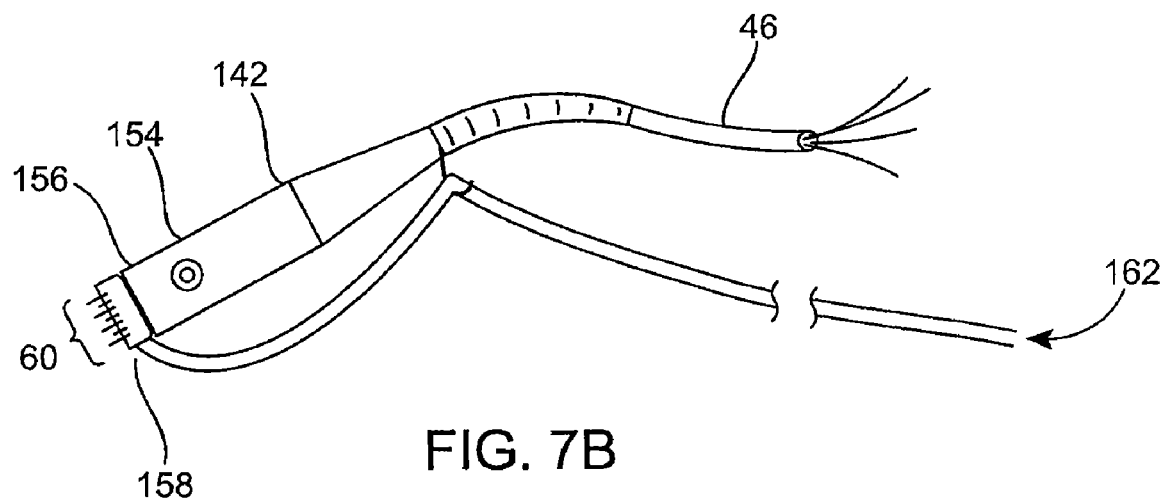

Referring now to FIGS. 7A and 7B a still further alternative system may include a proximal controller housing 140 and/or a probe applicator handpiece 142 as schematically illustrated. In this embodiment, controller housing 144 includes a receptacle for a cooling fluid cartridge 48 with the cooling fluid to cartridge being replaceable and having sufficient cooling fluid for at least a significant portion of a treatment of a single patient. The user interface of controller housing 144 includes a treatment time selector and/or indicator 146 and an indicator 148 which may generally indicate the treatment type or characteristics such as the treatment temperature, treatment efficacy duration, or the like.

Flexible body 46 extending between controller housing 144 and probe handpiece 142 includes a cooling fluid supply lumen 58, along with a thermal couple feedback 150, a heater power on/off switch conductor 152, and the like. Handpiece 142 includes a start button 154, and includes both a proximal housing 156 and a replaceable distal body 158. Body 158 includes an array of needles 160 as described above, and is detachably coupled to proximal body 156 and to a saline or other fluid infusion source 162. The fluid source 162 may comprise a pump, syringe, drip system, or the like and may provide a saline, a cryoprotectant, another biocompatible fluid, or the like. The fluid may be supplied warm from the fluid source 162 or maybe warmed at or adjacent body 158.

Figure 8A:
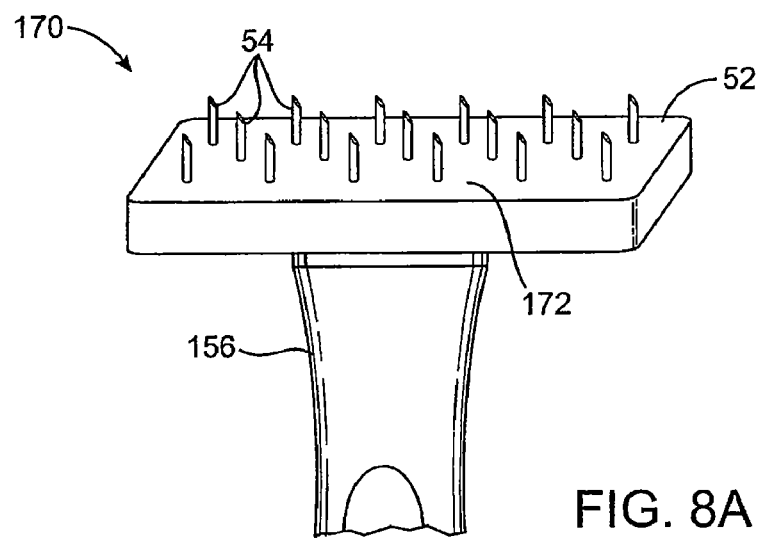
FIGS. 8A-8C illustrate a plurality of alternative treatment handpieces having a variety of different tissue-penetrating cooling probe arrays.
Figure 8B:
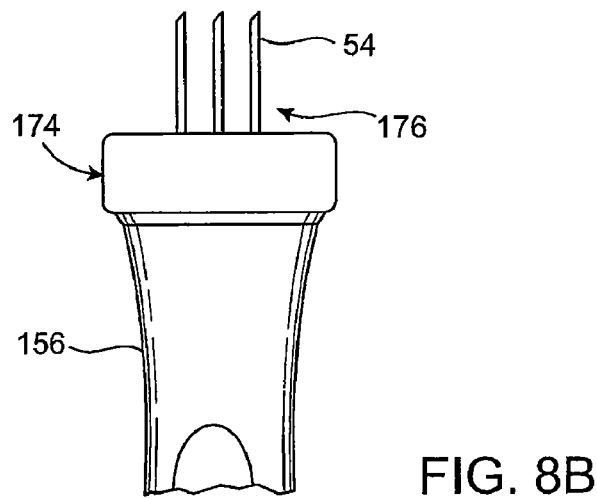
Figure 8C:
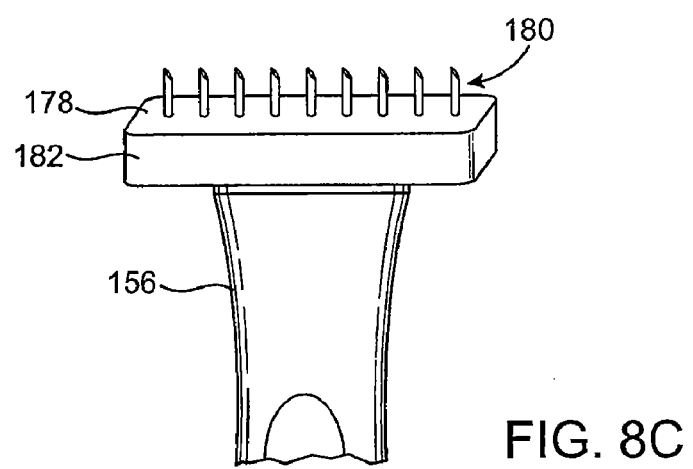

Referring now to FIGS. 8A-8C, a plurality of alternative probe handpiece bodies or heads of differing configurations may be provided. Probe head 170 includes an array of tissue-penetrating probes or needles 54 which are arranged to produced a treatment volume. A thermal sensor 172 on skin engaging surface 52 monitors skin temperature, and may be used to control a skin heater of the probe and/or the cooling treatment.

An alternative probe head 174 shown in FIG. 8B includes long tissue-penetrating probes 54 arranged in a linear array 176, and facilitates treatments along a plane, such as parallel to a bone. A still further alternative probe head 178 similarly includes a needle array 180 are ranged to produce a shallow treatment to plane or line. A probe head base 182 can be rigid (for example, being formed of stainless steel) or can be flexible to conform to the engaged skin or tissue surface (i.e., silicon). Resistive heating elements may be provided within probe head base, whether it is rigid or flexible. For example, a resistive heating element inside a silicon probe head base having about 2.5 watts per square inch of surface area may produce surface temperatures of approximately 45° C., suitable for warming a skin surface.

Figure 9:
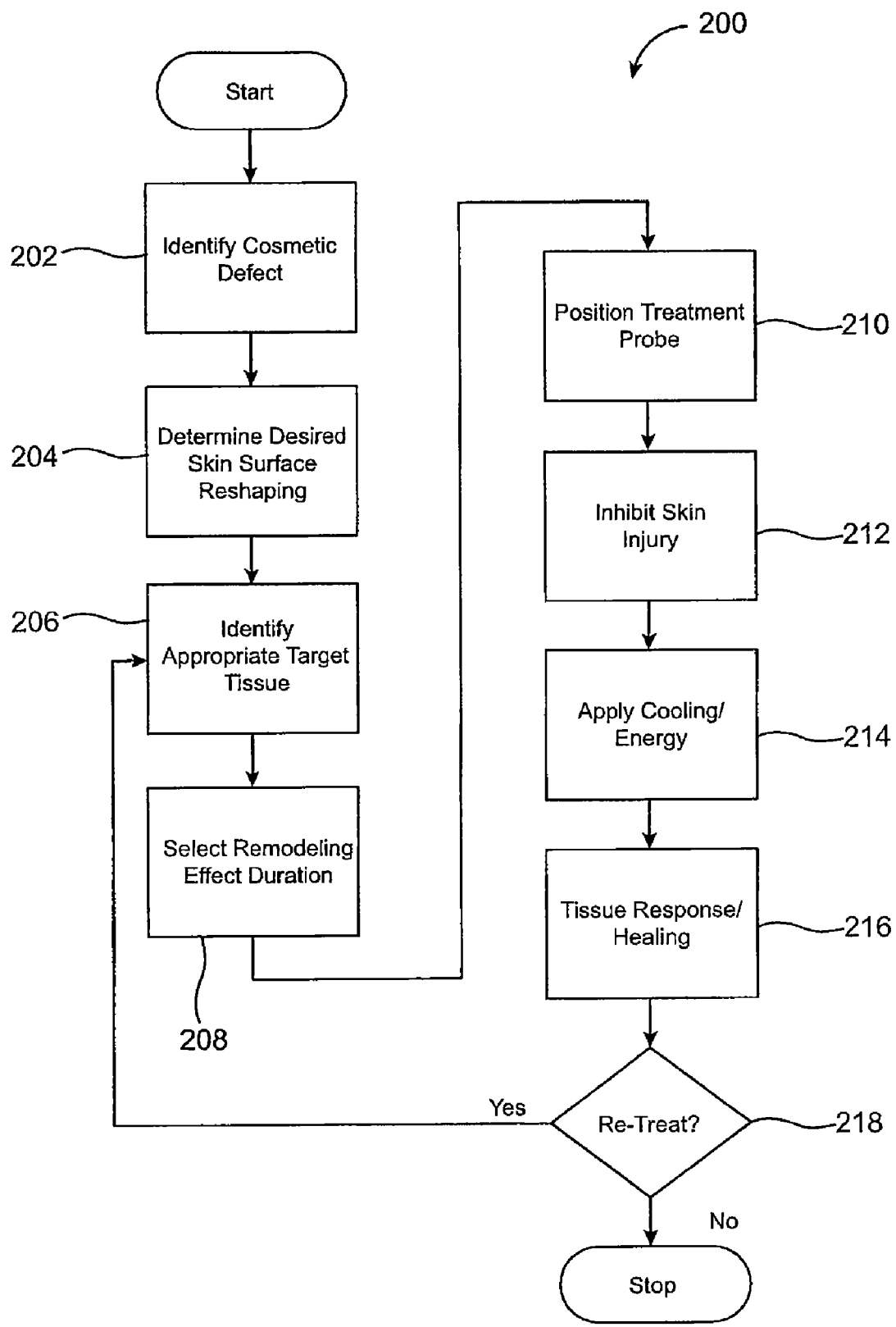
FIG. 9 is a flowchart schematically illustrating a method for cosmetically treating a target tissue disposed below a skin surface using cryogenic cooling so as to reshape the skin surface.

Referring now to FIG. 9, an embodiment of a method 200 for effecting a cosmetic treatment 200 includes identifying a cosmetic defect 202 such as lines, wrinkles, cellulite, fat, or the like. A desired skin surface reshaping is determined 204 which may include the elimination of lines or wrinkles, smoothing of cellulite dimples, reduction of fat, or the like. In many embodiments, it may be desirable to avoid permanently altering a color of the skin surface in effecting such treatments.

An appropriate target tissue is identified 206, such as identifying a nerve, muscle, neuromuscular junction, connective tissue, adipose tissue layer, or the like below the cosmetic defect. A remodeling effect duration 208 may be selected, and the treatment probe positioned 210. Positioning of the treatment probe may, for example, comprise inserting one or more tissue-penetrating probe needles into the target tissue, engaging the skin surface with a skin-engaging surface of a handpiece, and/or the like. Injury to the skin may be inhibited 212, such as by warming the skin surface, infusing a warmed biocompatible fluid such as saline, applying a cryoprotectant such as DMSO, or the like.

Cooling and/or energy (or chemical or vascular embolization) is applied to the target tissue 214 so as to effect the desired remodeling of that tissue. The tissue response and healing 216 may follow immediately after cooling and/or energy (or chemical or vascular embolization) is applied, or may take place over a considerable time (such as when efficacy is achieved through apoptosis or the like). If a short duration or trial treatment was performed to verify the target tissue and treatment effect, retreatment 218 may be performed.

While the exemplary embodiments have been described in some detail for clarity of understanding and by way of example, a number of modifications, changes, and adaptations may be implemented and/or will be obvious to those as skilled in the art. For example, one or more temperature feedback loops may be used to control the treatments, with the tissue temperature optionally being taken at varying tissue levels using (for example) the plurality of thermal couples advanced to varying depths of the tissue using a temperature sensing needle. Hence, the scope of the present invention is limited solely by the independent claims.

What is claimed is:

1. A system for treating tissue in a patient, said system comprising:
   a body comprising a handpiece having a size and a shape suitable for supporting
in a hand of an operator, and at least one cooling fluid supply path disposed in the handpiece;
   a probe attached to the handpiece, the probe comprising a probe body and an array of tissue penetrating needles attached thereto, wherein each tissue penetrating needle comprises a proximal portion, a distal portion, and a lumen therebetween fluidly coupled to the cooling fluid supply path, each tissue penetrating needle extending distally from the probe body and insertable into the tissue through a skin surface of the patient, the tissue comprising adipose tissue;
   a cooling fluid source coupleable to the fluid supply path to direct cooling fluid flow into the lumens of the tissue penetrating needles when cooling is initiated, so as to cool the tissue below the skin surface to remodel the adipose tissue and skin surface; and
   an electric heater element having a skin engaging surface, the heater element
adjacent the distal end of the probe body, the heater element directing heat energy into the skin to protect the skin from injury caused by the cooling
   wherein one or more of the needles comprise a fused silica supply tube extending into the lumen thereof.

2. The system of claim 1, further comprising a controller coupled to the cooling fluid supply path, the controller comprising instructions that, if executed, cause the system to direct a cooling energy into the tissue through the tissue penetrating needles, the cooling energy selected to remodel the adipose tissue and alter a surface of the patient's skin.

3. The system of claim 2, wherein the controller is configured to control at least one of treatment time or treatment temperature.

4. The system of claim 2, wherein the controller is configured to provide a treatment temperature of between about 0° C. to about −70° C.

5. The system of claim 2, wherein the controller is configured to deliver cooling energy selected to induce a reduction in adipose tissue mass.

6. The system of claim 1, further comprising a cooling fluid supply lumen extending distally within the probe.

7. The system of claim 1, further comprising a power source positioned within the body.

8. The system of claim 7, wherein the power source comprises a single-use battery or a rechargeable battery.

9. The system of claim 1, wherein the probe distal region is sealed such that the cooling fluid is prevented from leaking therefrom into the tissue.

10. The system of claim 1, wherein the cooling fluid source comprises a single-use canister.

11. The system of claim 1, wherein the cooling fluid source comprises a refillable canister.

12. The system of claim 1, wherein the electric heater element comprises a heating pad adapted to heat the patient's skin adjacent the probe.

13. The system of claim 1, further comprising a controller housing coupled to the body with a flexible body.

14. The system of claim 13, wherein the controller housing comprises a cooling fluid source fluidly coupled to the cooling fluid supply path.

15. The system of claim 1, wherein the tissue penetrating needles cool the tissue to a temperature in the range from about 0° C. to about −20° C.

* * * * *